(12) United States Patent
Buynak et al.

(10) Patent No.: US 6,407,091 B1
(45) Date of Patent: Jun. 18, 2002

(54) β-LACTAMASE INHIBITING COMPOUNDS

(75) Inventors: John D. Buynak, Dallas, TX (US); A. Srinivasa Rao, Waukegan, IL (US); Greg C. Adam, Dallas, TX (US); Sirishkumar D. Nidamarthy, Devon, PA (US); Venkata Ramana Doppalapudi, Dallas, TX (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/548,209

(22) Filed: Apr. 13, 2000

Related U.S. Application Data

(60) Provisional application No. 60/129,482, filed on Apr. 15, 1999.

(51) Int. Cl.[7] .................. A61K 31/545; A61P 31/04; C07D 501/00
(52) U.S. Cl. .................. 514/200; 514/202; 514/203; 514/204; 514/206; 514/207; 514/209; 540/215; 540/222; 540/225; 540/226; 540/228; 540/230
(58) Field of Search .................. 540/215, 222, 540/225, 226, 228, 230; 514/200, 202, 205, 204, 206, 207, 209

(56) References Cited

U.S. PATENT DOCUMENTS 5,760,027 A    6/1998    Buynak et al. .............. 514/200

FOREIGN PATENT DOCUMENTS

WO    96/17849    6/1996

OTHER PUBLICATIONS

Buynak, J.D., et al., "7–Alkylidenecephalosporin esters as Inhibitors of Human Leukocyte Elastase", *J. Med. Chem.*, vol. 40, pp. 3423–3433, (1997).

*Primary Examiner*—Mark L. Berch
(74) *Attorney, Agent, or Firm*—Schwegman, Lundberg, Woessner & Kluth, P.A.

(57) ABSTRACT

The invention provides compounds of formula I and IV:

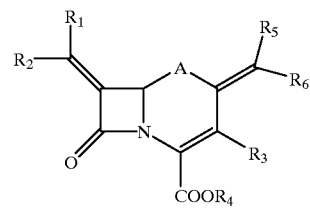

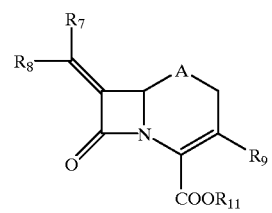

wherein $R_1$–$R_{11}$ and A have any of the values defined in the specification, and their pharmaceutically acceptable salts, are useful for inhibiting β-lactamase enzymes, for enhancing the activity of β-lactam antibiotics, and for treating β-lactam resistant bacterial infections in a mammal. The invention also provides pharmaceutical compositions, processes for preparing compounds of formula I and IV, and novel intermediates useful for the synthesis of compounds of formula I and IV. The A can be, for example, thio, sulfinyl, or sulfonyl.

35 Claims, 4 Drawing Sheets

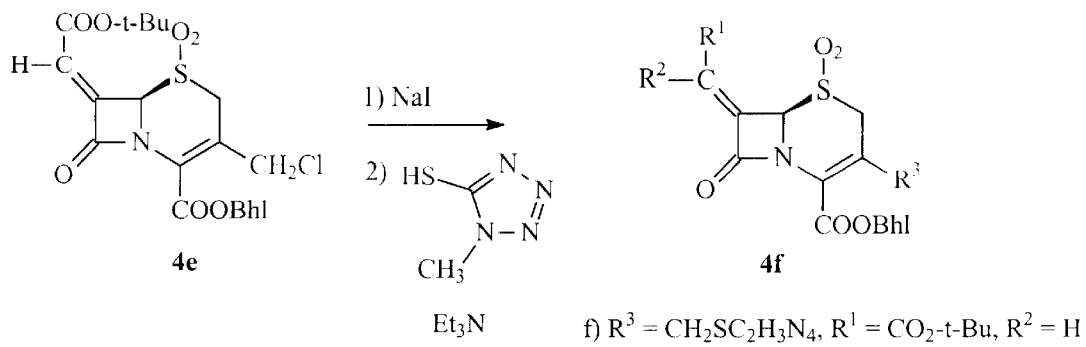

f) $R^3 = CH_2SC_2H_3N_4$, $R^1 = CO_2\text{-}t\text{-}Bu$, $R^2 = H$

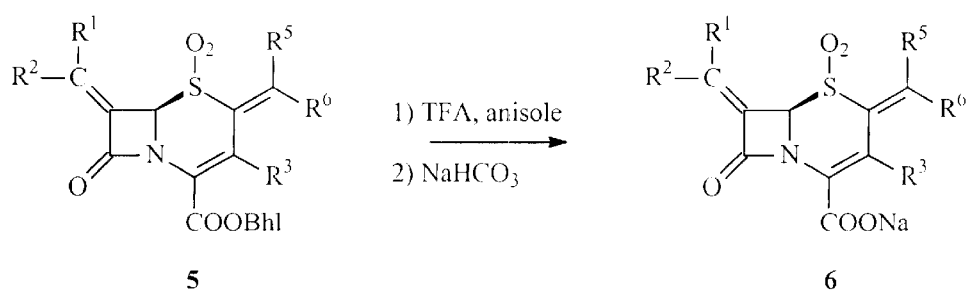

a) $R^3 = CH_2OAc$; $R^1 = 2'\text{-pyr}$; $R^2 = H$; $R^5, R^6 = H$
b) $R^3 = CH_2OAc$; $R^1 = CO_2\text{-}t\text{-}Bu$; $R^2 = H$; $R^5, R^6 = H$
c) $R^3 = CH_3$; $R^1 = 2'\text{-pyr}$; $R^2 = H$; $R^5, R^6 = H$
d) $R^3 = CH_3$, $R^1 = CO_2\text{-}t\text{-}Bu$, $R^2 = H$; $R^5, R^6 = H$
f) $R^3 = CH_2SC_2H_3N_4$, $R^1 = CO_2\text{-}t\text{-}Bu$, $R^2 = H$, $R^5, R^6 = H$
g) $R^3 = CH_3$, $R^1 = 2'\text{-pyr}$, $R^2 = H$; $R^5, R^6 = SCH_3$
h) $R^3 = CH_2OAc$; $R^1 = CO_2Na$; $R^2 = H$; $R^5, R^6 = H$
i) $R^3 = CH_3$, $R^1 = CO_2Na$, $R^2 = H$; $R^5, R^6 = H$

FIG. 2

β-LACTAMASE INHIBITING COMPOUNDS

RELATED APPLICATION

The invention described herein claims priority to U.S. Provisional Application Ser. No. 60/129,482, filed Apr. 15, 1999, under 35 U.S.C. 119.

BACKGROUND OF THE INVENTION

The most important mechanism of microbial resistance to β-lactam antibiotics is the bacterial production of β-lactamases, enzymes which hydrolytically destroy β-lactam antibiotics, such as penicillins and cephalosporins. This type of resistance can be transferred horizontally by plasmids that are capable of rapidly spreading the resistance, not only to other members of the same strain, but even to other species. Due to such rapid gene transfer, a patient can become infected with different organisms, each possessing the same β-lactamase.

β-lactamase enzymes have been organized into four molecular classes: A, B, C, and D based on amino acid sequence. Class A, which includes RTEM and the β-lactamase of *Staphylococcus aureus*, class C, which includes the lactamase derived from P-99 *Enterobacter cloacae*, and class D are serine hydrolases. Class A enzymes have a molecular weight of about 29 kDa and preferentially hydrolyze penicillins. The class B lactamases are metalloenzymes and have a broader substrate profile than the proteins in the other classes. Class C enzymes include the chromosomal cephalosporinases of Gram-negative bacteria and have molecular weights of approximately 39 kDa. The recently recognized class D enzymes exhibit a unique substrate profile which differs significantly from both class A and class C.

The class C cephalosporinases, in particular, are responsible for the resistance of gram negative bacteria to a variety of both traditional and newly designed antibiotics. The Enterobacter species, which possesses a class C enzyme, is now the third greatest cause of nosocomial infections in the United States. This class of enzymes often has poor affinities for inhibitors of the class A enzymes, such as clavulanic acid, a commonly prescribed inhibitor, and to common in vitro inactivators, such as 6-β-iodopenicillanate.

One strategy for overcoming this rapidly evolving bacterial resistance is the synthesis and administration of β-lactamase inhibitors. Frequently, β-lactamase inhibitors do not possess antibiotic activity themselves and are thus administered together with an antibiotic. One example of such a synergistic mixture is the product sold under the trademark AUGMENTIN (amoxicillin, clavulanate potassium), which contains the antibiotic amoxicillin and the β-lactamase inhibitor, clavulanate potassium.

There is a continued need for novel β-lactamase inhibitors, and in particular, for β-lactamase inhibitors that can be coadministered with a β-lactam antibiotic.

SUMMARY OF THE INVENTION

The invention provides a compound of formula I:

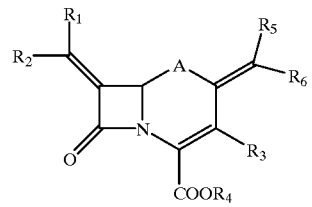

(I)

wherein:

$R_1$, $R_2$, $R_5$, and $R_6$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —COOR$_a$, —C(=O)NR$_b$R$_c$, —OC(=O)NR$_b$R$_c$, NR$_b$R$_c$, or —S(O)$_n$R$_d$; or $R_1$ and $R_2$ together with the carbon to which they are attached are $(C_3-C_8)$cycloalkyl or a heterocycle, wherein each $(C_3-C_8)$cycloalkyl or heterocycle is optionally substituted with $(C_1-C_{10})$alkyl, hydroxy, halo, $(C_1-C_{10})$alkoxy, $(C_1-C_{10})$alkanoyloxy, or $(C_1-C_{10})$alkoxycarbonyl; or $R_5$ and $R_6$ together with the carbon to which they are attached are $(C_3-C_8)$cycloalkyl or a heterocycle, wherein each $(C_3-C_8)$cycloalkyl or heterocycle is optionally substituted with $(C_1-C_{10})$alkyl, hydroxy, halo, $(C_1-C_{10})$alkoxy, $(C_1-C_{10})$alkanoyloxy, or $(C_1-C_{10})$alkoxycarbonyl;

$R_3$ is hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, halo, cyano, nitro, aryl, heterocycle, —COOR$_a$, —C(=O)NR$_b$R$_c$, —OC(=O)NR$_b$R$_c$, NR$_b$R$_c$, or —S(O)$_n$R$_d$;

$R_4$ is hydrogen;

A is thio (S), sulfinyl (SO), or sulfonyl (SO$_2$);

each n is independently 0, 1, or 2;

each R$_a$ is independently hydrogen, or $(C_1-C_{10})$alkyl;

each R$_b$ and R$_c$ is independently hydrogen, $(C_1-C_{10})$alkyl, $(C_1-C_{10})$alkoxy, phenyl, benzyl, phenethyl, or $(C_1-C_{10})$alkanoyl;

each R$_d$ is independently $(C_1-C_{10})$alkyl, $(C_1-C_{10})$alkanoyl, aryl, heterocycle, aryl$(C_1-C_6)$alkyl, heterocycle, or heterocycle$(C_1-C_6)$alkyl;

wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, or $(C_1-C_{10})$alkoxycarbonyl of $R_1$, $R_2$, $R_3$, $R_5$, and $R_6$ is optionally substituted with one or more (e.g. 1, 2, 3, or 4) substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$alkanoyloxy, aryloxy, (heterocycle)oxy, —COOR$_a$, $(C_3-C_8)$cycloalkyl, —C(=O)NR$_b$R$_c$, —OC(=O)NR$_b$R$_c$, NR$_b$R$_c$, and —S(O)$_n$R$_d$; and wherein any aryl is optionally substituted with one or more (e.g. 1, 2, 3, or 4) substituents independently selected from halo, hydroxy, cyano, trifluoromethyl, nitro, trifluoromethoxy, $(C_1-C_6)$ alkyl, $(C_1-C_6)$alkanoyl, $(C_1-C_6)$alkanoyloxy, $(C_1-C_6)$alkoxycarbonyl, —COOR$_a$, —C(=O)NR$_b$R$_c$, —OC(=O)NR$_b$R$_c$, NR$_b$R$_c$, and —S(O)$_n$R$_d$;

or a pharmaceutically acceptable salt thereof.

The invention also provides a compound of formula IV:

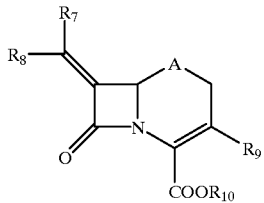

(IV)

wherein:

$R_7$ and $R_8$ are each independently hydrogen, $(C_1-C_{10})$ alkyl, $(C_2-C_{10})$alkenyl, $(C_2-C_{10})$alkynyl, $(C_3-C_8)$ cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$;

$R_9$ is cyano, —CH=NOR$_i$, or a radical of the following formula

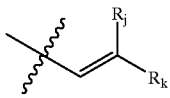

$R_{10}$ is hydrogen;

A is thio, sulfinyl, or sulfonyl;

each n is independently 0, 1, or 2;

each $R_e$ is independently hydrogen, or $(C_1-C_{10})$alkyl;

each $R_f$ and $R_g$ is independently hydrogen, $(C_1-C_{10})$ alkyl, $(C_1-C_{10})$alkoxy, phenyl, benzyl, phenethyl, or $(C_1-C_{10})$alkanoyl;

each $R_h$ is independently $(C_1-C_{10})$alkyl, phenyl, aryl $(C_1-C_6)$alkyl, heterocycle, or heterocycle$(C_1-C_6)$ alkyl;

$R_i$ is hydrogen or $(C_1-C_6)$alkyl; and $R_j$ and $R_k$ are each independently hydrogen, halo, cyano, nitro, aryl, heterocycle, $(C_2-C_6)$alkenyl, —COOR$_e$, —C(=O)NR$_f$R$_g$, —OC(=O)NR$_f$R$_g$, NR$_f$R$_g$, or —S(O)$_n$R$_h$;

wherein any $(C_1-C_{10})$alkyl, $(C_2-C_{10})$alkenyl, $(C_2-C_{10})$alkynyl, $(C_3-C_8)$cycloalkyl, $(C_1-C_{10})$ alkoxy, $(C_1-C_{10})$alkanoyl, $(C_1-C_{10})$alkanoyloxy, or $(C_1-C_{10})$alkoxycarbonyl of $R_7$, $R_8$, $R_j$ and $R_k$ is optionally substituted with one or more (e.g. 1, 2, 3, or 4) substituents independently selected from halo, hydroxy, cyano, cyanato, nitro, mercapto, oxo, aryl, heterocycle, $(C_2-C_6)$alkenyl, $(C_2-C_6)$ alkynyl, $(C_1-C_6)$alkoxy, $(C_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$ alkanoyloxy, aryloxy, (heterocycle)oxy, $(C_3-C_8)$ cycloalkyl, —COOR$_e$, —C(=O)NR$_f$R$_g$, —OC(=O)NR$_f$R$_g$, NR$_h$R$_i$, or —S(O)$_n$R$_k$; and wherein any aryl is optionally substituted with one or more (e.g. 1, 2, 3, or 4) substituents independently selected from halo, hydroxy, cyano, trifluoromethyl, nitro, trifluoromethoxy, $(C_1-C_6)$ alkyl, $(C_1-C_6)$alkanoyl, $(C_1-C_6)$alkanoyloxy, $(C_1-C_6)$alkoxycarbonyl, —COOR$_e$, —C(=O) NR$_f$R$_g$, —OC(=O)NR$_f$R$_g$, NR$_h$R$_i$, or —S(O)$_n$R$_k$;

or a pharmaceutically acceptable salt thereof.

The invention also provides a pharmaceutical composition comprising a compound of formula I or IV, or a pharmaceutically acceptable salt thereof, in combination with a pharmaceutically acceptable diluent or carrier, as well as such a pharmaceutical composition that further comprises a β-lactam antibiotic.

The invention also provides a method comprising inhibiting a β-lactamase by contacting (in vitro or in vivo) the β-lactamase with an effective amount of a compound of formula I or IV; or a pharmaceutically acceptable salt thereof.

The invention also provides a therapeutic method comprising inhibiting a β-lactamase in a mammal in need of such therapy, by administering an effective inhibitory amount of a compound of formula I or IV; or a pharmaceutically acceptable salt thereof.

The invention also provides a method comprising enhancing the activity of a β-lactam antibiotic, by administering the β-lactam antibiotic to a mammal in need thereof, in combination with an effective β-lactamase inhibiting amount of a compound of formula I or IV; or a pharmaceutically acceptable salt thereof.

The invention also provides a method comprising treating a β-lactam resistant bacterial infection in a mammal, by administering an effective amount of a β-lactam antibiotic in combination with an effective β-lactamase inhibiting amount of a compound of formula I or IV; or a pharmaceutically acceptable salt thereof.

The invention also provides a compound of formula I or IV for use in medical therapy (preferably for use in inhibiting a [-lactamase in a mammal, or for treating a β-lactam resistant bacterial infection in a mammal), as well as the use of a compound of formula I or IV for the manufacture of a medicament useful for inhibiting a β-lactamase in a human.

The invention also provides processes and intermediates disclosed herein that are useful for preparing β-lactamase inhibitors of formula I or IV.

Compounds of formula I and IV are useful as β-lactamase inhibitors for therapeutic applications. They are also useful as pharmacological tools for in vitro or in vivo studies to investigate the mechanisms of antibiotic resistance, to help identify other therapeutic antibiotic agents or β-lactamase inhibitors, to identify which β-lactamases are being expressed by a given microorganism, or to selectively inhibit one or more β-lactamases in a microorganism.

BRIEF DESCRIPTION OF THE FIGURES

FIG. 2 Illustrates the synthesis of compounds of formula I

DETAILED DESCRIPTION OF THE INVENTION

Figure 1:
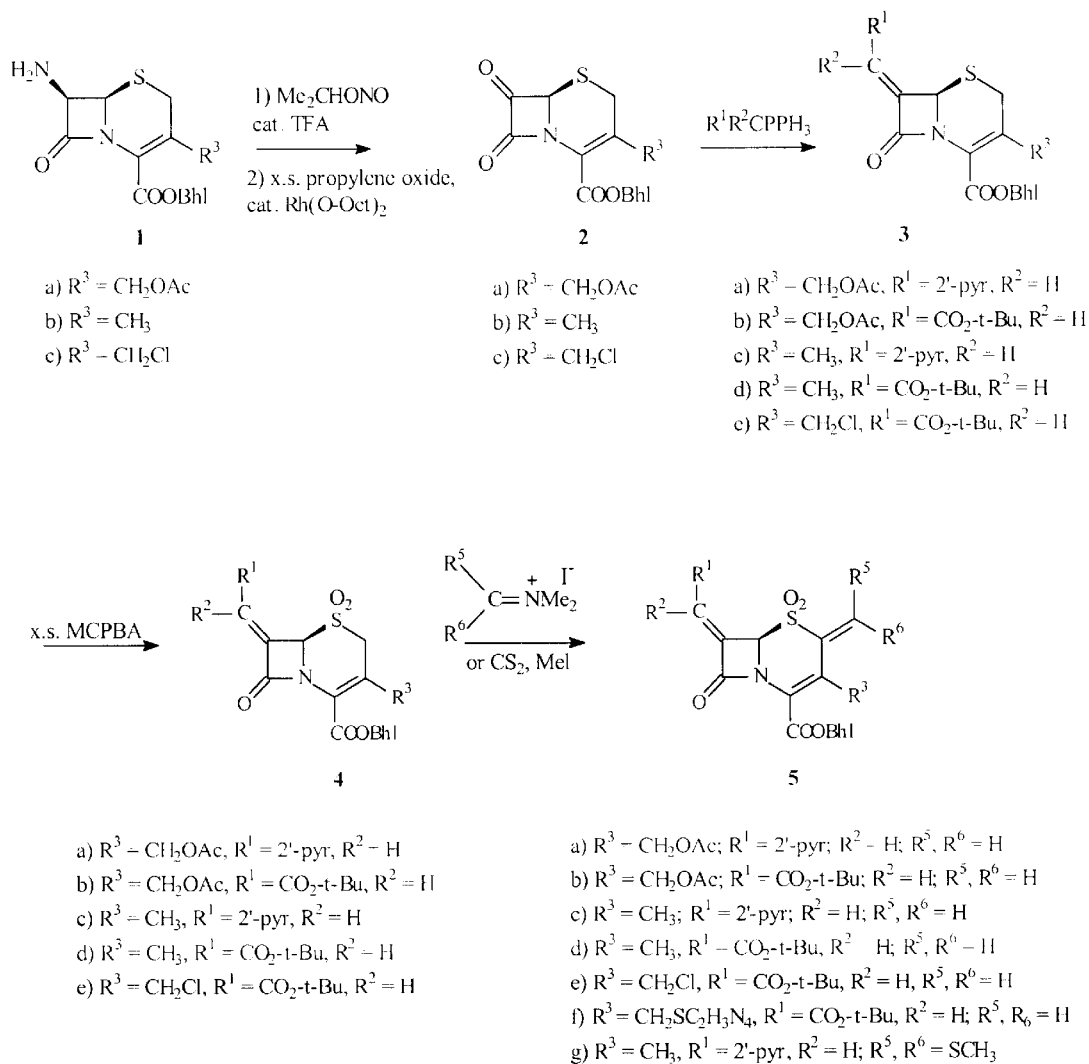
FIG. 1 Illustrates the synthesis of compounds of formula I

The following definitions are used, unless otherwise described: halo is fluoro, chloro, bromo, or iodo. Alkyl, alkoxy, alkenyl, etc. denote both straight and branched groups. Aryl denotes a phenyl radical or an ortho-fused bicyclic carbocyclic radical having about nine to ten ring atoms in which at least one ring is aromatic. Heterocycle denotes a 6–10 membered unsaturated or saturated mono- bi- or tri-cyclic ring system comprising carbon and 1, 2, 3, or 4 heteroatoms selected from the group consisting of non-peroxide oxygen, sulfur, and N(X) wherein each X is absent or is H, O, $(C_1-C_4)$alkyl, phenyl or benzyl. The term "heterocycle" includes "heteroaryl," which denotes a radical attached via a ring carbon of a monocyclic aromatic ring containing five or six ring atoms consisting of carbon and one to four heteroatoms each selected from the group consisting of non-peroxide oxygen, sulfur, and N(X) wherein each X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. The term "enhancing" the activity of a β-lactam antibiotic means improving or increasing the antibiotic activity of the compared in a statistically measurable and significant manner with respect to the activity demonstrated by the compound in the absence of a compound of the invention.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine β-lactamase inhibitory activity using the standard tests described herein, or using other similar tests which are well known in the art.

Specific values listed below for radicals, substituents and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_{10})$alkyl can be methyl, ethyl, propyl, isopropyl, butyl, iso-butyl, sec-butyl, pentyl, 3-pentyl, hexyl, heptyl, octyl, nonyl, or decyl; $(C_3-C_8)$cycloalkyl can be cyclopropyl, cyclobutyl, cyclopentyl, cyclohexyl, cycloheptyl, or cyclooctyl; $(C_1-C_{10})$alkoxy can be methoxy, ethoxy, propoxy, isopropoxy, butoxy, iso-butoxy, sec-butoxy, pentoxy, 3-pentoxy, hexyloxy, heptyloxy, octyloxy, nonyloxy or decyloxy; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_{10})$alkenyl can be vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl; $(C_2-C_6)$alkenyl can be vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_{10})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-dencynyl, 3-decynyl, 4-decynyl, 5-decynyl, 6-decynyl, 7-decynyl, 8-decynyl, or 9-decynyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_{10})$alkanoyl can be acetyl, propanoyl, butanoyl, pentanoyl, hexanoyl, heptanoyl, octanoyl, nonanoyl, or decanoyl; $(C_1-C_6)$alkanoyl can be acetyl, propanoyl, butanoyl, pentanoyl, hexanoyl; $(C_1-C_{10})$ alkoxycarbonyl can be methoxycarbonyl, ethoxycarbonyl, propoxycarbonyl, isopropoxycarbonyl, butoxycarbonyl, pentoxycarbonyl, hexyloxycarbonyl, heptyloxycarbonyl, octyloxycarbonyl, nonyloxycarbonyl or decyloxycarbonyl; $(C_1-C_{10})$alkanoyloxy can be formyloxy, acetoxy, propanoyloxy, butanoyloxy, isobutanoyloxy, pentanoyloxy, hexanoyloxy, heptanoyloxy, octanoyloxy, nonanoyloxy, or decanoyloxy; $(C_1-C_6)$alkanoyloxy can be formyloxy, acetoxy, propanoyloxy, butanoyloxy, isobutanoyloxy, pentanoyloxy, or hexanoyloxy; halo$(C_1-C_6)$alkanoyloxy can be iodoacetoxy, bromoacetoxy, chloroacetoxy, fluoroacetoxy, trifluoroacetoxy, 3-chloropropanoyloxy, 3-fluoropropanoyloxy, perfluoropropanoyloxy, or 3,3,3-trifluoropropanoyloxy; aryl can be phenyl, indenyl, or naphthyl; heterocycle can be triazolyl, triazinyl, oxazoyl, isoxazolyl, oxazolidinoyl, isoxazolidinoyl, thiazolyl, isothiazoyl, pyrazolyl, imidazolyl, pyrrolyl, pyrazinyl, pyridinyl, morpholinyl, quinolinyl, isoquinolinyl, indolyl, pyrimidinyl, piperidinyl, pyrrolidinyl, morpholinyl, thiomorpholinyl, or piperazinyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, 1-methyl-1H-tetrazol-5-yl, pyridyl, (or its N-oxide), thienyl, pyrimidinyl (or its N-oxide), indolyl, isoquinolyl (or its N-oxide) or quinolyl (or its N-oxide).

Specifically, $R_1$ is aryl, heterocycle, or —COOR$_a$.

Specifically, $R_1$ is 2-pyridyl, or —COOR$_a$.

Specifically, $R_2$ is hydrogen.

Specifically, $R_3$ is hydrogen, carboxy, or —CH$_2$M wherein M is hydrogen, halo, hydroxy, $(C_3-C_8)$cycloalkyl, $(C_1-C_6)$alkoxy, aryloxy, aryl$(C_1-C_{10})$alkoxy, mercapto, $(C_1-C_{10})$alkylthio, arylthio, heterocycle, (heterocycle)thio, $(C_1-C_{10})$alkanoylthio, aminocarbonyloxy, or NR$_b$R$_c$. More specifically, M is hydrogen, halo, $(C_1-C_{10})$alkanoyloxy, or heterocycle.

Specifically, $R_3$ is acetoxymethyl, phenylacetoxymethyl, (3,4-dihydroxyphenyl)acetoxymethyl, chloromethyl, formyl, or chloroacetoxymethyl.

Specifically, $R_3$ is hydrogen, methyl, acetoxymethyl, or 1-methyl-1H-tetrazol-5-ylthiomethyl.

Specifically, $R_3$ is vinyl, optionally substituted at the 2-position with halo, cyano, —COOR$_a$, trifluoromethyl, formyl, $(C_3-C_8)$cycloalkyl, $(C_2-C_6)$alkenyl, $(C_2-C_6)$alkynyl, heterocycle, or NR$_b$R$_c$.

Specifically, $R_3$ is vinyl, optionally substituted at the 2-position with cyano, —COOR$_a$, $(C_2-C_6)$alkenyl, or heteroaryl.

Specifically, A is sulfonyl (—SO$_2$—).

Specifically, $R_7$ is aryl, heterocycle, or —COOR$_e$.

Specifically, $R_7$ is 2-pyridyl, or —$COOR_e$.

Specifically. $R_8$ is hydrogen.

Specifically, $R_j$ and $R_k$ are each independently hydrogen, cyano, —$COOR_e$, ($C_2$–$C_{10}$)alkenyl, or heteroaryl.

More specifically $R_1$ is carboxy, 2-pyridyl, tert-butoxycarbonyl, or methoxycarbonyl.

More specifically, $R_3$ is 2-cyanovinyl, 2-(methoxycarbonyl)vinyl, 2-(2-pyridyl-N-oxide)vinyl, or 1,3-butadienyl.

More specifically, $R_5$ and $R_6$ are each individually hydrogen.

More specifically, $R_5$ and $R_6$ are each individually methylthio.

More specifically, $R_j$ and $R_k$ are each independently hydrogen, cyano, 2-(methoxycarbonyl), 2-pyridyl-N-oxide, or vinyl.

A specific compound is a compound of formula I wherein A is sulfonyl (—$SO_2$—); $R_1$ is 2-pyridyl, carboxy or tert-butoxycarbonyl; $R_2$ is hydrogen; $R_3$ is hydrogen, methyl, acetoxymethyl or 1-methyl-1H-tetrazol-5-ylthiomethyl; and $R_5$ and $R_6$ are the same and are each hydrogen or thiomethyl; or a pharmaceutically acceptable salt thereof.

A specific compound is a compound of formula IV wherein A is sulfonyl (—$SO_2$—); $R_7$ is 2-pyridyl, carboxy or tert-butoxycarbonyl; $R_8$ is hydrogen; and $R_9$ is 2-cyanovinyl, 2-(methoxycarbonyl)vinyl, 2-(2'-pyridyl-N-oxide)vinyl, or 1,3-butadienyl; or a pharmaceutically acceptable salt thereof.

A preferred compound of formula I or IV is a pharmaceutically acceptable salt formed from a carboxylic acid of formula I or IV wherein $R_4$ or $R_{10}$ is hydrogen. Most preferred is a salt wherein $R_4$ or $R_{10}$ been replaced with a sodium or potassium ion. The term pharmaceutically acceptable salts also includes poly salts (e.g. di- or tri-salts) of a compound of formula I or IV, particularly a dicarboxylic acid salt of a compound of formula I wherein $R_1$ is carboxy and $R_4$ is hydrogen, or a dicarboxylic acid salt of a compound of formula IV wherein $R_7$ is carboxy and $R_{10}$ is hydrogen Processes and novel intermediates useful for preparing compounds of formula I and IV are provided as further embodiments of the invention and are illustrated by the following procedures in which the meanings of the generic radicals are as given above unless otherwise qualified. Additional compounds of the present invention, processes of making compounds of the present invention, and/or intermediates of compounds of the present invention are disclosed in Buynak et al., *Bioorg. Med. Chem. Lett.*, 2000, 10 4211 and Buynak et al., *Bioorg. Med. Chem. Lett.*, 2000, 10 4215.

Pharmaceutically acceptable salts of compounds of formula I wherein $R_4$ has been replaced with a pharmaceutically acceptable cation (e.g. a sodium or potassium ion) can conveniently be prepared from a corresponding compound of formula I wherein $R_4$ is hydrogen, by reaction with a suitable base, for example, as disclosed in Example 1 hereinbelow.

Pharmaceutically acceptable salts of compounds of formula IV wherein $R_{10}$ has been replaced with a pharmaceutically acceptable cation (e.g. a sodium or potassium ion) can conveniently be prepared from a corresponding compound of formula IV wherein $R_{10}$ is hydrogen, by reaction with a suitable base.

A useful intermediate for preparing a compound of formula I or IV, herein $R_4$ or $R_{10}$ is hydrogen, is a corresponding compound wherein $R_4$ or $R_{10}$ has been replaced with a suitable removable carboxy protecting group. Such protecting groups are well known in the art, for example, see Greene, T. W.; Wutz, P. G. M. "Protecting Groups In Organic Synthesis" second edition, 1991, New York, John Wiley & Sons, Inc. Preferred protecting groups include ($C_1$–$C_{10}$) alkyl, ($C_2$–$C_{10}$)alkenyl, ($C_3$–$C_8$)cycloalkyl, ($C_2$–$C_{10}$) alkynyl, aryl, benzyl, or benzhydryl. Thus the invention provides compounds of formula I wherein $R_1$, $R_2$, $R_3$, $R_5$, and $R_6$ have any of the values, specific values, or preferred values defined herein, and wherein $R_4$ is ($C_1$–$C_{10}$)alkyl, ($C_2$–$C_{10}$)alkenyl, ($C_3$–$C_8$)cycloalkyl, ($C_2$–$C_{10}$)alkynyl, aryl, benzyl, or benzhydryl. The invention also provides compounds of formula IV wherein $R_7$, $R_8$, and $R_9$ have any of the values, specific values, or preferred values defined herein, and wherein $R_{10}$ is ($C_1$–$C_{10}$)alkyl, ($C_2$–$C_{10}$)alkenyl, ($C_3$–$C_8$)cycloalkyl, ($C_2$–$C_{10}$)alkynyl, aryl, benzyl, and benzhydryl.

Compounds of formula (I) can be prepared as shown in FIG. 1 by esterifying 7-aminocephalosporanic acid (commercially available from Aldrich) with diphenyldiazomethane to produce benzhydryl 7-aminocephalosporinate compound 1. Treatment with isoamyl nitrite in the presence of a catalytic amount of TFA at room temperature gives the corresponding diazo compound which is treated directly with propyleneoxide and a catalytic amount of rhodium(II) octanoate dimer in benzene to give the corresponding benzhydryl 7-oxocephalosporinate compound 2. The degree of purity can be enhanced by substituting isoamylnitrite with isopropylnitrite and rhodium(II)acetate with rhodium(II) octonate.

7-Alkylidenecephalosporinates 3 can be prepared by treating benzhydryl 7-oxocephalosporinate with the requisite Wittig Reagent. Oxidation of the resulting compound for example with an excess amount of 70% m-CPBA in methylene chloride and phosphate 6.4 buffer, gives the corresponding sulfone 4 that can be treated with Eschenmoser's salt in acetonitrile to give ester 5. Hydrolysis of the ester followed by salt formation under standard conditions, for example, as illustrated in the Examples hereinbelow and in FIG. 2, gives a compound 6.

The invention also provides intermediates of formulae 2, 3, 4, and 5, wherein $R_1$, $R_2$, $R_3$, $R_5$, and $R_6$ have any of the values, specific values, or preferred values defined herein, and wherein "Bhl" is diphenylmethyl or is another suitable carboxy protecting group such as for example ($C_1$–$C_{10}$) alkyl, ($C_2$–$C_{10}$)alkenyl, ($C_3$–$C_8$)cycloalkyl, ($C_2$–$C_{10}$) alkynyl, aryl, or benzyl, that are useful to prepare compounds of formula I.

Figure 3:
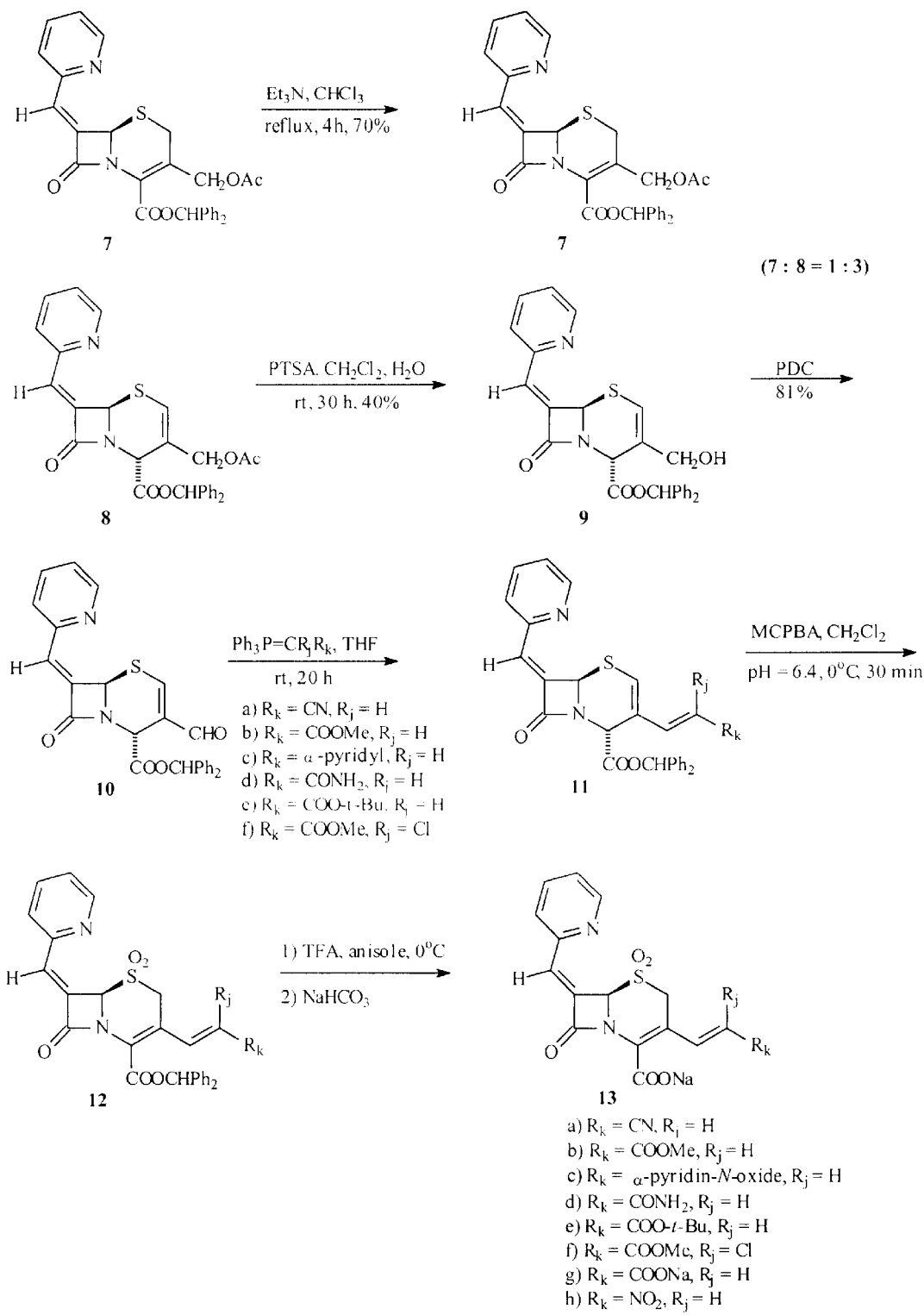
FIG. 3 Illustrates the synthesis of compounds of formula IV
Figure 4:
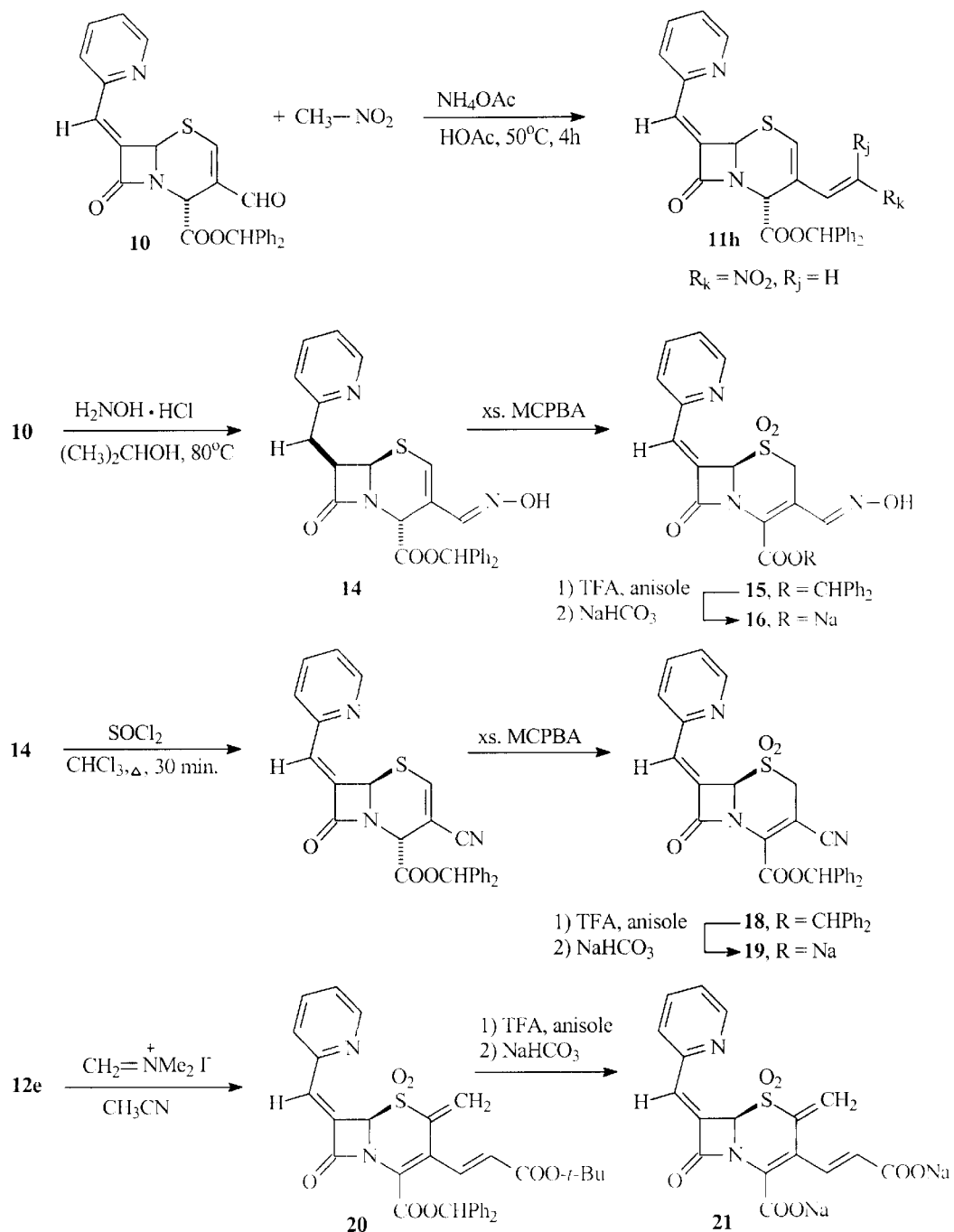
FIG. 4 Illustrates the synthesis of compounds of formulae I and IV

As illustrated in FIG. 3, compounds of formula IV (e.g. wherein $R_7$ is 2-pyridyl and $R_8$ is hydrogen) can be prepared from compound 7, which is available from 2, using procedures similar to those described by J. D. Buynak et. al., *J. Med. Chem.* 38, 1022–1034, 1995. Thus, 7 is isomerized to a 1:3 mixture of 7 and 8, respectively. Compound 8 is separated and hydrolyzed to alcohol 9, which is oxidized to provide aldehyde 10. Reaction of 10 with a series of ylides provides compounds 11a through 11f. Compound 10 can also be condensed with nitromethane to produce nitroalkene 11h (FIG. 4), or can be reacted with hydroxylaiminie hydrochloride, to produce oxime 14 (FIG. 4), which itself can be reacted with thionyl chloride to generate nitrile 17. Oxidation of compounds 11a–11f, 11h, 14, and 17 yields the corresponding sulfones. Compound 12e can also be reacted with Eschenmoser's salt to generate sulfone 20 (FIG. 4). Hydrolysis of the esters 12a–12f, 12h, 15, 18, and 20 (e.g. with trifluoroacetic acid (TFA) in anisole) yields the carboxylate salts 13a–13f, 13h, 16, 19, and 21, which are active as β-lactamase inhibitors. Compound 13 g was prepared by hydrolysis of compound 12e.

A compound that is particularly useful for preparing a compound of formula IV is an aldehyde of formula V:

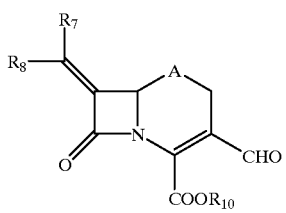

(V)

wherein $R_7$, $R_8$, $R_{10}$, and A have any of the values, specific values, or preferred values described herein.

Compounds of formula I wherein $R_1$ and $R_2$ are alkoxy or alkene may be synthesized using an appropriate Wittig reagent $R_1R_2C=PP_3$. The Wittig reagents $ROCH=PPh_3$, $H_2C=CH—CH=PPh_3$, and similar reagents may also be used to make the 7-alkoxymethylene and 7-alkenylmethylene compounds, respectively.

The 7-alkanoylmethylene species may be made by forming the vinyl anion and reacting it with a desirable alkanoyl halide. The vinyl anion may be made by a standard lithium-halogen (or magnesium-halogen) exchange reaction, for example, reaction of compound 4a with methyl lithium. The lithium vinyl group may then be functionalized by reaction with an alkoxycarbonyl chloride.

2- or 7-Carboxylmethylene compounds ($R_1$, $R_2$, $R_5$, or $R_6$=COOH) may be formed by hydrolysis of a corresponding ester, preferably, the corresponding t-butyl ester.

Compounds wherein $R_3$ is a halogen may be formed by displacement of an acetoxy group with ethyl xanthate (EtOCS$_2$K), followed by Raney-Nickel desulfurization (H$_2$/Ra—Ni) to give the exocyclic alkene, which can be ozonized to the 3-hydroxy cephem. Reaction of the hydroxy compound with a halogenating reagent gives the 3-halo species. For example, PCl$_5$, may be used to convert the 3-OH group into a 3-Cl group.

Compounds wherein $R_3$ is a hydrogen may be formed by reduction of the aforementioned 3-hydroxy cephem to the corresponding 3-hydroxy cepham with sodium borohydride. Subsequent treatment with methanesulfonyl chloride in the presence of triethylamine results in elimination of the hydroxyl group generating the compound in which $R_3$ is hydrogen.

Compounds wherein $R_3$ is methyl, can be obtained from the commercially available starting material 7-amino-3-desacetoxycephalosporin using a sequence similar to that illustrated in FIG. 1.

Compounds wherein $R_3$ is 3-hydroxymethyl may be obtained by hydrolysis of a corresponding acetoxy group (e.g. with NaOH or an appropriate enzyme).

Compounds wherein $R_3$ is halomethyl may be formed by reaction of a corresponding 3-hydroxymethyl compound with a halogenating reagent. For example, PCl$_5$ may be used to form the 3-chloromethyl species.

Compounds wherein $R_3$ is alkoxymethyl, aryloxymethyl, or arylalkoxymethyl may be obtained by reaction of the corresponding 3-hydroxymethyl compound with tosyl chloride and displacement of the resultant tosylate with an oxide. For example, sodium methoxide may be used to obtain the 3-methoxymethyl species.

Compounds wherein $R_3$ is mercaptomethyl may be formed by reaction of a corresponding 3-chloromethyl compound with sodium sulfhydride (NaSH). This compound may further be derivatized with an alkylhalide to form a alkylthio group, or an acylchloride to form an acylthio group, for example, as described in Jerry March "Advanced Organic Chemistry" John Wiley & Sons, 4 ed. 1992, 407.

Compounds wherein $R_3$ is aminomethyl may be formed by the Gabriel Synthesis, i.e., reaction of the corresponding 3-chloromethyl compound with potassium phthalimide followed by hydrolysis of the product with acid to yield the 3-aminomethyl compound.

A compound of formula I wherein $R_3$ is hydroxymethyl may also be prepared from a corresponding compound of formula I wherein $R_3$ is chloroacetoxymethyl by treatment with thiourea in the presence of a suitable base, such as for example, pyridine (T. Greene, P. Wutz "Protective Groups in Organic Synthesis, Second Edition; John Wiley and Sons, Inc.; New York, 1991, p. 92).

A compound of formula I wherein $R_3$ is cyanomethyl can be prepared from a corresponding compound of formula I wherein $R_3$ is halomethyl using techniques that are well known in the art, for example techniques such as those described in Jerry March "Advanced Organic Chemistry" John Wiley & Sons, 4 ed. 1992, 482.

A compound of formula I wherein $R_3$ is —CH$_2$NR$_b$R$_c$ can be prepared from a corresponding compound of formula I wherein $R_3$ is —CH$_2$(halo) using techniques that are well known in the art, for example techniques such as those described in Jerry March "Advanced Organic Chemistry" John Viley & Sons, 4 ed. 1992, 411–413, 425–427.

A compound of formula I wherein $R_3$ is formyl can be prepared from a corresponding compound of formula I wherein $R_3$ is hydroxymetlhyl by oxidation, using techniques which are well known in the art.

A compound of formula I wherein $R_3$ is a 1-alkenyl substituent can generally be prepared from a corresponding compound of formula I wherein $R_3$ is formyl, by reaction with the requisite ylide or stabilized ylide, using techniques which are well known in the art.

A compound of formula I wherein $R_3$ is cyanatomethyl can be prepared from a corresponding compound of formula I wherein $R_3$ is hydroxymethyl by reaction with a cyanogen halide using techniques that are well known in the art, for example techniques such as those described in Jerry March "Advanced Organic Chemistry" John Wiley & Sons, 4 ed. 1992, 387.

Compounds wherein $R_3$ is aminocarbonylmethyl can be formed by displacement of the corresponding tosylate with cyanide, e.g., KCN, followed by hydrolysis of the resulting nitrile to the amide.

A compound of formula I or IV wherein A is sulfonyl (—SO$_2$—) can be prepared by oxidation of a corresponding compound of formula I or IV wherein A is thio (—S—), for example, by using meta-chloroperbenzoic acid (mCPBA).

A compound of formula I or IV wherein A is sulfinyl (—SO—) can be prepared by oxidation of a corresponding compound of formula I or IV wherein A is thio (—S—), using one equivalent of an acceptable oxidizing agent, for example, mCPBA.

Another useful intermediate for the preparation of a compound of the invention is an ylide, for example a ylide of formula $R_1R_2C=PPh_3$, $R_5R_6C=PPh_3$, or $R_jR_kC=PPh_3$. Ylides can be prepared using techniques that are well known in the art, for example techniques such as those described in Jerry March "Advanced Organic Chemistry" John Wiley & Sons, 4 ed. 1992, 956–963. Suitable ylides are also disclosed in U.S. Pat. No. 5,597,817, issued Jan. 29, 1997; and U.S. Pat. No. 5,629,306, issued May 13, 1997.

Compounds of formula I and IV wherein A is —S— or —SO— are particularly useful as intermediates for preparing the corresponding compounds of formula I or IV wherein A is —SO2—.

Many of the starting materials employed in the synthetic methods described above are commercially available or are reported in the scientific literature. It may be desirable to optionally use a protecting group during all or portions of the above described synthetic procedures. Such protecting groups and methods for their introduction and removal are well known in the art. See Greene, T. W.; Wutz, P. G. M. "Protecting Groups In Organic Synthesis" second edition, 1991, New York, John Wiley & Sons, Inc.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula I can be formulated as pharmaceutical compositions and administered to a mammalian host, such as a human patient in a variety of forms adapted to a selected route of administration, i.e., by oral, parenteral, intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as prescervatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or chicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antiifungal agents, for example, parabens, chlorobutanol. phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The present compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

For veterinary medicine, the composition may, for example, be formulated as an intramammary preparation in either long acting or quick-release bases.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The compositions per unit dosage, whether liquid or solid may contain from 0.1% to 99% of active material (the present 7-vinylidene cephalosporins and optional antibiotic), the preferred range being from about 10–60%. The composition will generally contain from about 15 mg to about 1500 mg by weight of active ingredient based upon the total weight of the composition; however, in general, it is preferable to employ a dosage amount in the range of from about 250 mg to 1000 mg. In parenteral administration the unit dosage is usually the pure compound in a slightly acidified sterile water solution or in the form of a soluble powder intended for solution. Single dosages for injection, infusion or ingestion may be administered, i.e., 1–3 times daily, to yield levels of about 0.5–50 mg/kg, for adults.

The invention provides a pharmaceutical composition, comprising an effective amount of a compound of formula I or IV as described hereinabove; or a pharmaceutically acceptable salt thereof; and a pharmaceutically acceptable carrier. The invention also provides a pharmaceutical composition comprising an effective amount of a compound of formula I or IV as described hereinabove; or a pharmaceutically acceptable salt thereof, a β-lactam antibiotic; and a pharmaceutically acceptable carrier. The present compositions are preferably presented in a form suitable for absorption by the gastro-intestinal tract.

Any β-lactam antibiotic is suitable for use in the pharmaceutical composition of the invention. β-lactam antibiotics which are well known in the art include those disclosed by R. B. Morin and M. Gorin, M.Eds.; Academic Press, New York, 1982; vol. 1–3. Preferred β-lactam antibiotics, suitable for use in the pharmaceutical composition of the invention, include β-lactam antibiotics which are preferentially deactivated by Class A and Class C β-lactamase enzymes, for example, amoxicillin, piperacillin, ampicillin, ceftizoxime, cefotaxime, cefuroxime, cephalexin, cefaclor, cephaloridine, and ceftazidime.

The ability of a compound of the invention to function as a β-lactamase inhibitor can be demonstrated using the test described below, or using other tests which are well known in the art. Representative compounds of formula I were evaluated as inhibitors of the Class C β-lactamase of *Enterobacter cloacae* P-99, a cephalosporinase, and TEM-1, a penicillinase, by relative $IC_{50}$ analysis. The $IC_{50}$ value represents the concentration of inhibitor required to effect a 50% loss of activity of free enzyme. The $IC_{50}$ value of each compound was determined as follows. Following a 10 minute incubation of a dilute solution of enzyme (2.56 nM) and inhibitor (<0.64 mM), a 50 mL aliquot of this incubation mixture was then further diluted into 1 mL nitrocefin solution, and the rate of hydrolysis was measured during a 1 minute period by monitoring the absorbance of nitrocefin as a function of time. In addition, the $IC_{50}$ values of tazobactam were determined as relative controls. The data is presented in Table 1 below for compounds of the formulae I, II, and III.

TABLE 1

$IC_{50}$ Values for Inhibition of β-lactam23ase (µM) Derived from P-99 or TEM-1 (relative to tazobactum standard)

| No. | type | R1 | R2 | R3 | R4 | R5 | R6 | P-99 | TEM-1 |
|---|---|---|---|---|---|---|---|---|---|
|  | tazo |  |  |  | Na |  |  | 74.5 | 0.243 |
| 6a | I | 2-pyr | H | $CH_2OAc$ | Na | H | H | 0.165 | 99.2 |
| 6b | I | $CO_2$-t-Bu | H | $CH_2OAc$ | Na | H | H | 1.55 | 0.932 |
| 6c | I | 2-pyr | H | $CH_3$ | Na | H | H | 0.039 | 91.1 |
| 6d | I | $CO_2$-t-Bu | H | $CH_3$ | Na | H | H | 48.6 | 56.5 |
| 6f | I | $CO_2$-t-Bu | H | $CH_2S(C_2N_4H_3)$ | Na | H | H | 2.38 | 1.13 |
| 6g | I | 2-pyr | H | $CH_3$ | Na | $SCH_3$ | $SCH_3$ | 0.51 | 172.8 |
| 6h | I | $CO_2Na$ | H | $CH_2OAc$ | Na | H | H | 2.49 | 498 |
| 6i | I | $CO_2Na$ | H | $CH_3$ | Na | H | H | 36.8 | 277 |
|  | II | 2-pyr | H | $CH_3$ | Na |  |  | 6.10 | 377 |
|  | II | 2-pyr | H | $CH_2OAc$ | Na |  |  | 1.35 | 14.4 |
|  | II | $CO_2$-t-Bu | H | $CH_3$ | Na |  |  | 199 | 111.2 |
|  | II | $CO_2$-t-Bu | H | $CH_2OAc$ | Na |  |  |  |  |

TABLE 1-continued

IC$_{50}$ Values for Inhibition of β-lactam23ase (μM) Derived from P-99 or TEM-1
(relative to tazobactum standard)

| No. | type | R1 | R2 | R3 | R4 | R5 | R6 | P-99 | TEM-1 |
|---|---|---|---|---|---|---|---|---|---|
| | II | CO$_2$-t-Bu | H | CH$_2$S(C$_2$N$_4$H$_3$) | Na | | | 112 | 0.123 |
| | III | | | CH$_2$OAc | Na | H | H | 315 | >2000 |

Compounds of formuale II and III are provided for comparison purposes. Compounds of formula I generally possess activity as β-lactamase inhibitors, and, thus, are useful as therapeutic agents and as pharmacological tools as described herein. Compounds of formulae II and III are generally less effective against P-99 than corresponding compounds of formula I. In general, compounds of formula I are more potent toward P-99 than is tazobactam, showing a 1 to 2000 fold

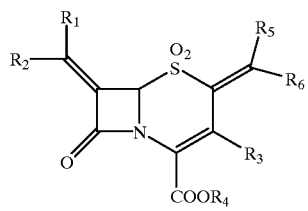

I

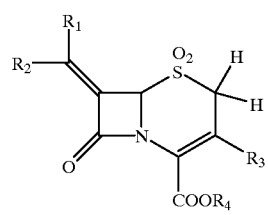

II

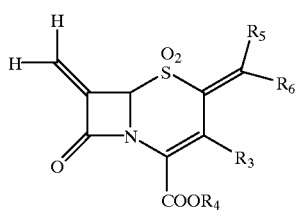

III increase in activity. Many compounds of formula I also show activity toward TEM-1.

Representative compounds of formula IV were also evaluated as inhibitors of the Class C β-lactamase of *Enterobacter cloacae* P-99, a cephalosporinase, and TEM-1, a penicillinase, by relative IC$_{50}$ analysis using a procedure similar to that described above. The data is presented in Table 2 below.

TABLE 2

IC$_{50}$ Values (μM) for Inhibition of β-lactamase Derived from P-99 or TEM-1

| No | P-99 | TEM-1 |
|---|---|---|
| 13a | 0.01 | 2.7 |
| 13b | 0.2 | 0.02 |
| 13c | 0.6 | 0.006 |
| 13e | 1.48 | — |
| 13f | 0.2 | 0.02 |
| 13g | 0.31 | 2.52 |
| 19 | 0.029 | 2.34 |

The present β-lactamase inhibitors of formulae I and IV are particularly useful in the treatment of infections associated with Enterobacter, Citrobacter, and Serratia. These bacteria have the ability to attach to the epithelial cells of the bladder or kidney (causing urinary tract infections) and are resistant to multiple antibiotics including amoxicillin and ampicillin.

The present β-lactamase inhibitors of formula I are also be useful in the treatment of infections associated with highly resistant Pneumococci. Such diseases include otitis media, sinusitis, meningitis (both in children and adults), bacteremia, and septic arthritis. Resistant pneumococcal strains have surfaced in many parts of the world. For example, in Hungary, 58% of *S. pneumoniae* are resistant to penicillin, and 70% of children who are colonized with *S. pneumoniae* carry resistant strains that are also resistant to tetracycline, erythromycin, trimethoprin/sulfamethoxazole (TMP/SMX), and 30% resistant to chloramphenicol. *Klebsiella pneumoniae* (resistant via the production of β-lactamase) have caused hospital outbreaks of wound infection and septicemia.

Other features of the invention will become apparent in the course of the following descriptions of exemplary embodiments which are given for illustration of the invention and are not intended to be limiting thereof.

EXAMPLES

Example 1

Sodium Salt of 7-[(Z)-(2'-Pyridyl)methylene]-2-(exomethylidene)cephalosporanic Acid Sulfone (6a)

To a solution of ester 5a (1.0 g, 1.43 mmol) in anisole at 0° C. was added trifluoroacetic acid ("TFA") and the reaction mixture was stirred for 10 minutes. TFA and anisole were removed in vacuo and the residue was dissolved in EtOAc and extracted into aqueous sodium bicarbonate. The aqueous layer was loaded onto reverse phase column and eluted with 5% ethanol/water to give compound 6a (0.58 g, 79%). $^1$H NMR (400 MHZ, D$_2$O): δ 8.41 (d, J=4.53 Hz), 7.68 (t, J=7.84 Hz, 1H), 7.37–7.39 (m, 1H), 7.35 (s, 1H), 7.23–7.26 (m, 1H), 6.33 (s, 1H), 6.13 (s, 1H), 6.03 (s, 1H), 4.94 (s, J=12.73 Hz, 1H), 4.58 (d, J=12.8 Hz, 1H), 1.86 (s, 3H).

The intermediate ester 5a was prepared as follows.

a. Benzhydryl 7-Oxocephalosporinate (2a). To a solution of benzhydryl 7-aminocephalosporinate (0.5 g, 0.15 mmol) (which can be prepared in one step from the commercially available 7-aminocephalosporanic acid according to procedures described in Buynak et. al. *J. Am. Chem. Soc.* 116, 10955–10965, 1994) in ethyl acetate (5 mL) were added isopropyl nitrite (0.38 mL, 1.71 mmol, 40% solution in $CH_2Cl_2$) and trifluoroacetic acid (6.5 mg, 0.05 mmol) and the reaction was allowed to stir for 1 hour at room temperature. The reaction mixture was concentrated under reduced pressure and redissolved in benzene (5 mL). To this solution was added propylene oxide (6.7 g, 0.114 mol) followed by rhodium octanoate dimer (5 mg) and the reaction was stirred for 15 minutes (until evolution of nitrogen ceases). Volatiles were removed to produce the title compound 2a (0.5 g, quantitative, 90% pure); IR ($CHCl_3$) 3005, 1830, 1790, 1740 $cm^{-1}$; $^1H$ NMR ($CDCl_3$) δ 7.39 (10H, m), 7.05 (1H, s), 5.32 (1H, s), 5.07 (1H, d, A of ABq, J=13.9 Hz), 4.85 (1H, d, B of ABq, J=14.0 Hz), 3.64 (1H, d, A of ABq, J=18.5 Hz), 3.44 (1H, d, B of ABq, J=18.6 Hz), 2.05 (3H, s); $^{13}C$ NMR ($CDCl_3$) 188.4 (s), 170.3 (s), 160.1 (s), 158.7 (s), 138.8 (s), 138.6 (s), 128.4, 128.2, 128.1, 127.7, 126.9. 126.2, 80.1 (d), 65.8 (d), 62.6 (t), 27.7 (t), 20.4 (q).

b. Benzhydryl 7-[(Z)-(2'-Pyridyl)methylene]cephalosporinate (3a). To a solution of 2-picolyl chloride hydrochloride (13.1 g, 80 mmol) in water (20 mL) was added into potassium carbonate (11.0 g, 80 mmol). After the carbonate was completely dissolved, the solution was extracted with ether (3×10 mL). The combined organic layers were washed with saturated NaCl solution (1×30 mL), dried ($Na_2SO_4$) and concentrated to give picolyl chloride (9.2 g, 90%). Picolyl chloride (8.9 g, 70 mmol), triphenylphosphine (18.3 g, 70 mmol) and 1,4-dioxane (30 mL) were mixed and refluxed for 24 hours. The reaction mixture was washed with ether (2×30 mL) and the remaining solid was dried in vacuo to give a white solid (25.5 g, 94%). A mixture of 2-picolyltriphenylphosphonium chloride (5.8 g, 15 mmol) and sodium amide (0.58 g, 15 mmol) in THF (15 mL) was stirred at room temperature for 30 minutes. The resulting brown suspension was cooled to −78° C. and a solution of benzhydryl 7-oxocephalosporinate 2a (6.6 g, 15 mmol) in THF (15 mL) was added in one portion and the mixture was stirred at −78° C. for 15 minutes. The reaction was quenched by the addition of saturated ammonium chloride solution (10 mL) and extracted with EtOAc (2×20 mL). The combined organic layers were washed with water (2×40 mL), dried over $MgSO_4$, concentrated and purified by column chromatography to obtain a 3a as a yellow solid (2.9 g, 38%). $R_f$=0.28 in 2% EtOAc in $CH_2Cl_2$; mp 181–183° C.; IR ($CHCl_3$) 3060, 1810, 1750 $cm^{-1}$, $^1H$ NMR ($CDCl_3$) δ 8.68 (1H, d), 7.72 (1H, t), 7.35 (12H, m), 7.15 (1H, s), 7.10 (1H, s), 5.66 (1H, s), 4.96 (1H, d, A of ABq, 13 Hz), 4.73 (1H, d, B of ABq, J=13 Hz), 3.63 (1H, d, A of ABq, J=18 Hz), 3.63 (1H, D, B of ABq, J=18 Hz), 2.01 (3H, s); $^{13}C$ NMR ($CDCl_3$) δ 170.3 (s), 161.0 (s), 160.2 (s), 151.6 (d), 150.1 (s), 140.6 (s), 139.3 (s), 139.1 (s), 136.6 (d), 128.3, 127.9, 127.8, 127.6, 127.2, 126.9, 125.8 (s), 123.9 (s), 123.5 (s), 79.5 (d), 63.0 (t), 58.5 (d), 28.0 (t), 20.5 (q); high-resolution mass spectrum for $[C_{29}H_{24}N_2O_5SNa]^+$, i.e. $[M+Na]^+$, m/z calcd 535.1304, found 535,1300.

c. Benzhydryl 7-[(Z)-(2'-Pyridyl)methylene]cephalosporinate Sulfone (4a). To a solution of sulfide 3a (0.45 g, 0.88 mmol) in $CH_2Cl_2$ (10 mL) and pH=6.4 Buffer solution (10 mL) was added m-CPBA (85%, 0.71 g, 3.52 mmol) in one portion. The mixture was stirred at room temperature for 30 minutes, and then ether (50 mL) was added. After separating layers, the organic layers were washed with saturated $NaHCO_3$ (3×30 mL), dried ($NaSO_4$), concentrated and purified by column chromatography to yield a white solid (yield=90%); $R_f$=0.26 in 2% EtOAc in $CH_2Cl_2$; mp 120–122° C.; IR ($CHCl_3$) 2975, 2950, 1780, 1720, 1340, 1130 $cm^{-1}$; $^1H$ NMR ($CDCl_3$) δ 8.67 (1H, d), 7.71 (1H, t), 7.40 (13H, m), 7.00 (1H, s), 5.91 (1H, s), 5.14 (1H, d, A of ABq, J=14 Hz), 4.80 (1H, B of ABq, J=14 Hz), 4.11 (1H, d, A of ABq, J=18 Hz), 3.78 (1H, d, B of ABq, J=18 Hz), 2.05 (3H, s); high-resolution mass spectrum for $[C_{29}H_{24}N_2O_7SNa]^+$, i.e. $[M+Na]^+$, m/z calcd 567.1202, found 567.1198.

d. Benzhydryl 7-[(Z)-(2"-Pyridinyl)methylene]-2-(exomethylidene)cephalosporinate Sulfone (5a). To a solution of sulfone 4a (0.75 g, 1.37 mmol) in dry $CH_3CN$ (10 mL) at 0° C. was added Eschenmoser's salt (0.57 g, 3.06 mmol) and the reaction was stirred for 3 hours. $CH_3CN$ was then removed under reduced pressure and the reaction mixture was dissolved in $CH_2Cl_2$ (30 mL) and washed with water (2×30 mL) and brine. The organic layer was dried over $Na_2SO_4$ and concentrated under reduced pressure to give 697 mg (91%) of 5a; $^1H$ NMR (400 MHZ, $CDC_3$) δ 8.68 (d, J=5.01 Hz, 1H), 7.73 (t, J=5.99 Hz, 1H), 7.42–7.31 (m, 10H), 7.05 (s, 1H), 6.67 (s, 1H), 6.16 (s, 1H), 6.04 (s, 1H), 5.20 (d, J=12.95 Hz, 1H), 4.63 (d, J=12.95 Hz), 1.95 (s, 3H).

Example 2

Sodium Salt of 7-[(Z)-(tert-Butoxycarbonyl)methylene]-2-(exomethylidene)cephalosporinate Sulfone (6b).

To a solution of ester 5b (0.68 g, 1.16 mmol) in anisole (3.79 mL, 34.9 mmol) at 0° C. was added TFA (10.8 mL, 139 mmol) and the reaction mixture stirred for 10 minutes. TFA and anisole were removed in vacuo and the residue was dissolved in EtOAc and extracted into a solution of $NaHCO_3$ (0.146 g/10 mL $H_2O$). The aqueous layer was then loaded onto reverse phase column chromatography and compound 6j eluted with water and the compound 6b eluted with 5% EtOH/water; $^1H$ NMR (400 MHZ, $D_2O$) δ 6.65 (s, 1H), 6.40 (s, 1H), 6.07 (s, 1H), 5.82 (s, 1H), 4.98 (d, J=10.87 Hz, 2H), 1.89 (s, 3H).

The intermediate ester 5b was prepared as follows.

a. Benzhydryl 7-[(Z)-t-butoxycarbonylmethylene]cephalosporinate (3b). To a solution of benzhydryl 7-oxocephalosporinate 2a (4.0 g, 9.2 mmol) in anhydrous $CH_2Cl_2$ (40 mL) at −78° C. was added a solution of methyl(triphenylphosphoranylidene)acetate (3.45 g, 9.15 mmol in 40 mL $CH_2Cl_2$). The mixture was then stirred at −78° C. for 30 minutes. Acetic acid (1 mL) was added to quench the reaction and the reaction mixture was concentrated and purified by column chromatography to give compound 3b as a pale yellow solid (55%); $R_f$=0.52 in 2% EtOAc in $CH_2Cl_2$; mp 48–50° C.; IR ($CHCl_3$) 3050, 1780, 1730 $cm^{-1}$; $^1H$ NMR ($CDCl_3$) δ 7.36 (10H, m), 7.00 (1H, s), 6.39 (1H, s), 5.47 (1H, s), 5.00 (1H, d, A of ABq, J=13.48 Hz), 4.77 (1H, d, B of ABq, J=13.48 Hz), 3.62 (1H, d, A of ABq, J=18 Hz), 3.38 (1H, d, B of ABq, J=18 Hz), 2.02 (3H, s), 1.54 (9H, s); $^{13}C$ NMR ($CDCl_3$) δ 170.2 (s), 162.4 (s), 160.5 (s), 157.8 (s), 150.1 (s), 139.0 (s), 138.8 (s), 128.3, 128.0, 127.9, 127.5, 126.9, 125.0 (s), 119.9 (d), 82.9 (s), 79.7 (d), 62.8 (t), 57.5 (d), 28.0 (q), 27.9 (t), 20.4 (q). Anal. Calcd for $C_{29}H_{29}NO_7S$: C, 65.05; H, 5.42; N, 2.62. Found: C, 64.50; H, 5.42, N, 2.62.

b. Benzhydryl 7-[(Z)-(t-butoxycarbonyl)methylene] cephalosporanate Sulfone (4b). This compound was prepared from the corresponding sulfide 3b using a procedure similar to that described in Example 1 suβ-part c, to give a white solid (73%); $R_f$=0.68 in 5% EtOAc in $CH_2Cl_2$; mp 58–60° C.; IR ($CHCl_3$) 3025, 1800, 1730, 1350, 1160 $cm^{-1}$; $^1$H NMR ($CDCl_3$) δ 7.36 (10 H, m), 6.98 (1H, s), 6.59 (1H, s), 5.58 (1H, s), 5.14 (1H, d, A of ABq, J=14 Hz), 4.80 (1H, d, B of ABq, J=14 Hz), 4.12 (1H, d, A of ABq, J=18 Hz), 3.77 (1H, d, B of ABq, J=18 Hz), 2.04 (3H, s), 1.52 (9H, s); $^{13}$C NMR ($CDCl_3$) δ 170.0 (s), 161.5 (s), 159.4 (s), 157.1 (s), 142.3 (s), 138.6 (s), 138.5 (s), 128.8, 128.4, 128.3, 127.2, 127.0, 125.9 (s), 123.5 (d), 83.8 (s), 80.2 (d), 71.6 (d), 61.3 (t), 52.8 (t), 27.6 (q), 20.2 (q); high-resolution mass spectrum for $[C_{29}H_{29}NO_9SNa]^+$, i.e. $[M+Na]^+$, m/z calcd 590.1461, found 590.1447.

c. Benzhydryl 7-[(Z)-(tert-butoxycarbonyl)methylene]-2-(exomethylidene)cephalosporinate Sulfone (5b). To a solution of sulfone 4b (0.7 g, 1.22 mmol) in dry $CH_3CN$ (10 mL) at 0° C. was added Eschenmoser's salt (0.45 g, 2.43 mmol) and the reaction was stirred for 3 hours. $CH_3CN$ was then removed under reduced pressure and the reaction mixture was dissolved in $CH_2Cl$, (20 mL) and washed with water (2×30 mL). The organic layer was dried over $Na_2SO_4$ and concentrated under reduced pressure to give compound 5b (680 mg, 96%); $^1$H NMR (400 MHZ, $CDCl_3$) δ 7.41–7.25 (m, 10H), 7.0 (s, 1H), 6.71 (s, 1H), 6.6 (s, 1H), 6.2 (s, 1H), 5.6 (s, 1H), 5.26 (d, J=13.0 Hz, 1H), 4.68 (d, J=13 Hz, 1H), 1.56 (s, 3H).

Example 3

Sodium Salt of 7-((Z)-(2"-Pyridinyl)methylene]-3'-desacetoxy-2-(exomethylidene)cephalosporinate Sulfone (6c)

To a solution of ester 5c (0.3 g, 0.597 mmol) in anisole (1.94 g, 64.5 mmol) at 0° C. was added TFA (8.17 g, 71.7 mmol) and the reaction stirred for 10 minutes. TFA and anisole were removed in vacuo and the residue was dissolved in ethyl acetate (10 mL). The compound was extracted into an aqueous solution of $NaHCO_3$. The aqueous layer was loaded onto a column of the high porous polymer CHP20P (MitsubishI Chemical Corp., White Plains, N.Y.) eluted with 5% EtOH/water to give compound 6c (0.17 g, 80%); $^1$H NMR (400 MHZ, $D_2O$)δ 8.55 (d, J=5.2 Hz, 1H), 7.83 (t, J=7.66 Hz, 1H), 7.61 (d, J=7.63 Hz, 1H), 7.46 (s, 1H), 7.38–7.41 (m, 1H), 6.43 (s, 1H), 6.25 (s, 1H), 6.11 (s, 1H), 1.94 (s, 3H).

The intermediate 5c was prepared as follows.

a. Benzhydryl 7-Oxo-3'-(desacetoxy)cephalosporinate (2b). To a solution of benzhydryl 7-amino-3'-(desacetoxy) cephalosporinate (15 g, 39.5 mmol) in ethyl acetate (300 mL) were added isopropyl nitrite (13.3 mL, 59.2 mmol, 40% solution in $CH_2Cl_2$) and trifluoroacetic acid (0.13 g, 1.18 mmol) and the reaction was allowed to stir for 1 hour at room temperature. The reaction mixture was concentrated under reduced pressure and redissolved in benzene (75 mL). To this solution was added propylene oxide (150 mL) followed by rhodium octanoate dimer (100 mg) and the reaction was stirred for 15 n-tin (until evolution of nitrogen ceases). Volatiles were removed to produce compound 2b (15 g, quantitative, >90% pure); $^1$H NMR ($CDCl_3$) δ 7.97–7.25 (10H, m), 6.99 (1H, s), 5.29 (1H, s), 3.47 (1H, d, A of ABq, J=17.9 Hz), 3.29 (1H, d, B of ABq, J=17.9 Hz), 2.18 (3H, s).

b. Benzhydryl 7-(Z)-[(2'-Pyridyl)methylene]-3'-desacetoxy cephalosporinate (3c). To a solution of potassium t-butoxide (3.16 g, 28.3 mmol) in dry THF (40 mL) was added (2'-picolinyl)triphenylphosphonium chloride (11.6 g, 29 mmol) and the reaction was stirred for 60 minutes. This freshly generated ylide was added to a cold (−78° C.) solution of ketone 2b via cannula and the reaction was stirred for 45 minutes at the same temperature. The reaction mixture was quenched with a saturated solution of $NH_4Cl$ (50 mL) and extracted with ether (250 mL). The organic layer was then dried over $Na_2SO_4$ and concentrated under reduced pressure to give 3c (3.6 g ). $^1$H NMR (400 MHZ, $CDCl_3$) δ 8.67 (d, 1H), 7.29 (d, 1H), 7.52 (2H), 7.50–7.25 (m, 10H), 7.10 (s, 1H), 6.9 (s, 1H), 5.65 (s, 1H), 3.47 (d, J=18.0 Hz, 1H), 3.19 (d, J=18.0 Hz, 1H), 2.10 (s, 3H).

c. Benzhydryl 7-(Z)-[(2'-Pyridinyl)methylene]-3'-(desacetoxy) cephalosporinate Sulfone (4c). To a solution of sulfide 3c (2 g, 4.39 mmol) in $CH_2Cl_2$ (25 mL) was added m-CPBA (70%) (3 g, 17.6 mmol) and phosphate 6.4 buffer (25 mL) and the resulting solution was stirred for 1 hour. The reaction mixture was diluted with $CH_2Cl_2$ and the organic layer was washed with $Na_2SO_3$ (2×30 mL) followed by $NaHCO_3$ (2×25 mL), extracted with $CH_2Cl_2$ (50 mL), dried over sodium sulphate, concentrated under reduced pressure, and purified by silica gel column chromatography to give 4c (71%); $^1$H NMR (400 MHZ, $CDCl_3$) δ 8.67 (d, 1H), 7.71 (d, 1H), 7.49 (2H), 7.39–7.25 (m, 10H), 6.9 (s, 1H), 5.7 (s, 1H), 3.86 (d, J=16.6 Hz, 1H), 3.79 (d, J=16.6 Hz, 1H), 2.2 (s, 3H).

d. Benzhydryl 7-[(Z)-(2"-pyridinyl)methylene]-3'-desacetoxy-2-(exomethylidene)cephalosporinate Sulfone (5c). To a solution of sulfone 4c (0.75 g, 1.53 mmol) in dry $CH_3CN$ (10 mL) at 0° C. was added Eschenmoser's salt (0.57 g, 3.06 mmol) and the reaction was stirred for 3 hours. $CH_3CN$ was then removed under reduced pressure and the reaction mixture was dissolved in $CH_2Cl_2$ (30 mL) and washed with water (2×30 mL) and brine. The organic layer was dried over $Na_2SO_4$ and concentrated under reduced pressure to give compound 5c (720 mg, 93%); $^1$H NMR (400 MHZ, $CDCl_3$) δ 8.69 (d, J=0.88 Hz, 1H), 7.73 (t, J=8 Hz, 1H), 7.47–7.31 (m, 12H), 7.04 (s, 1H), 6.67 (s, 1H), 6.05 (s, 1H), 6.01 (s, 1H), 2.07 (s, 3H).

Example 4

Sodium Salt of 7-[(Z)-(tert-Butoxycarbonyl) methylene]-3'-desacetoxy-2(exomethylidene) cephalosporinate Sulfone (6d)

To a solution of ester 5d (0.3 g, 0.572 mmol) in anisole (1.86 mL, 17.2 mmol) at 0° C. was added TFA (2.65 mL, 34.3 mmol) and the reaction stirred for 10 minutes. TFA and anisole were removed in vacuo and the residue was dissolved in EtOAc (10 mL). The compound was extracted into a solution of $NaHCO_3$ (0.072 g, 0.858 mmol). The aqueous layer was loaded onto a column of the high porous polymer CHP20P (MitsubishI Chemical Corp., White Plains, N.Y.) and elution with water to give the disalt 6k. Elution with 5% EtOH/$H_2O$ gave the mono salt 6d; δ 6.45 (s, 1H), 5.79 (s, 1H), 1.71 (s, 3H), 1.30 (s, 9H).

The intermediate 5d was prepared as follows.

a. Benzhydryl-7-[(Z)-(tert-butoxycarbonyl)methylene]-3'-(desacetoxy)cephalosporinate (3d). To a solution of 2b (5 g, 1.31 mmol) in dry THF at −78° C. was added a solution of (tert-butoxycarbonylmethylene)triphenylphosphorane (4.9 g, 1.04 mmol) slowly and the reaction stirred for 1 hour at the same temperature under nitrogen. The reaction mixture was then quenched with a saturated solution of $NH_4Cl$ (75 mL) and the compound was extracted into $CH_2Cl_2$ (75 mL). The organic layer was dried over $Na_2SO_4$, concentrated under reduced pressure, and purified by silica gel chromatography to give 3d (3.9 g, 62%); $^1H$ NMR, 400 MHZ, $CDCl_3$, δ 7.48–7.26 (m, 10H), 6.95 (s, 1H), 6.34 (s, 1H), 5.45 (s, 1H), 3.48 (d, J=18.1 Hz, 1H), 3.22 (d, J=18.1 Hz, 1H), 2.12 (s, 3H), 1.52 (s, 9H).

b. Benzhydryl 7-[(tert-butoxy)methylene]-3'-(desacetoxy) cephalosporinate Sulfone (4d). To a solution of sulfide 3d (2 g, 4.16 mmol) in $CH_2Cl_2$ (25 mL) was added m-CPBA (70%) (4 g, 23.2 mmol) and phosphate 6.4 buffer (25 mL) and the reaction stirred for 1 hour at room temperature. The reaction mixture was then diluted with $CH_2Cl_2$ and the organic layer was washed with $Na_2SO_3$ (2×20 mL) followed by $NaHCO_3$ (2×25 mL). The product was extracted into $CH_2Cl_2$, dried over sodium sulphate, concentrated under reduced pressure, and purified by silica gel column chromatography to give compound 4d (1.5 g, 71%); $^1H$ NMR, 400 MHZ, $CDCl_3$, δ 7.46–7.26 (m, 10H), 6.94 (s, 1H), 6.54 (s, 1H), 5.40 (s, 1H), 3.86 (d, J=16.8 Hz, 1H), 3.73 (d, J=16.8H z, 1H), 2.17 (s, 3H), 1.54 (s, 9H).

c. Benzhydryl 7-[(Z)-(tert-butoxycarbonyl)methylene]-3'-desacetoxy-2-(exomethylidene)cephalosporinate Sulfone (5d). To a solution of sulfone 4d (0.475 g, 0.92 mmol) in dry $CH_3CN$ (10 mL) at 0° C. was added Eschenmoser's salt (0.685 g, 2.76 mmol) and the reaction mixture stirred at this temperature for 3 hours. $CH_3CN$ was removed under reduced pressure and the residue was dissolved in $CH_2Cl_2$ and washed with water. The organic layer was dried over $Na_2SO_4$ and concentrated under reduced pressure to give compound 5d (0.31 g, 63.7%); $^1H$ NMR (400 MHZ, $CDCl_3$) δ 7.43–7.26 (m, 10H), 7.0 (s, 1H), 6.7 (s, 1H), 6.59 (s, 1H), 6.13 (s, 1H), 5.65 (s, 1H), 2.17 (s, 3H), 1.53 (s, 9H).

Example 5

Sodium Salt of Benzhydryl 7-[(Z)-(tert-Butylcarboxy)methylene]-3'-desacetoxy-2-exomethylidene-3'-[1"-methyl-1"H-tetrazol-5"-yl) thio]cephalosporinate Sulfone (6f)

To a solution of compound 5f (0.22 g, 0.34 mmol) in anisole (1.13 mL, 10.2 mmol) at 0° C. was added TFA (1.6 mL) and the reaction was stirred for 10 minutes. TFA and anisole were removed in vacuo. The residue was dissolved in EtOAc and the compound was extracted into an aqueous solution of $NaHCO_3$ (0.043 g, 0.51 mmol). The aqueous layer was loaded onto a column of the high porous polymer CHP20P (MitsubishI Chemical Corp., White Plains, N.Y.) and eluted with 5% $EtOH/H_2O$ to give compound 6f; $^1H$ NMR (400 MHZ, $D_2O$) δ 6.66 (s, 1H), 6.60 (s, 1H), 6.31 (s, 1H), 6.10 (s, 1H), 4.41 (d, J=13.7 Hz, 1H), 3.94 (s, 3H), 1.43 (s, 9H).

The intermediate compound 5f was prepared as follows.

a. Benzhydryl (3-Chloromethyl)-7-oxocephalosporinate (2c). To a solution of benzhydryl 7-amino-3-(chloromethyl)cephalosporinate (4 g, 9.7 mmol) in EtOAc (100 mL) was added isoamylnitrite (1.55 mL, 11.6 mmol) and a catalytic amount of TFA (20l) and the resulting solution was allowed to stir for 25 minutes. Volatiles were removed under reduced pressure to give a yellow solid which was identified as 7-diazo compound. The yellow solid was then dissolved in benzene (25 mL) and propylene oxide (50 mL, 1164 mmol) was added followed by rhodium octanoate (50 mg). The reaction mixture was stirred for 10 minutes and then concentrated under reduced to obtain ketone 2c as a yellow solid; $^1H$ NMR ($CDCl_3$, 400 MHZ), δ 7.45–7.35 (m, 10H), 7.0 (s, 1H), 5.3 (s, 1H), 4.34 (d, J=13.8 Hz, 1H), 4.37 (d, J=13.8 Hz, 1H), 3.69 (d, J=18 Hz, 1H), 3.56 (d, J=18 Hz, 1H).

b. Benzhydryl 7-[(Z)-(tert-butoxycarbonyl)methylene]-3'-chloro 3'-(desacetoxy)cephalosporinate (3e). To a solution of ketone 2c (3.87 g, 9.41 mmol) in dry THF at −78° C. was added a solution of 1-tert-butoxycarbonylmethylene-triphenylphosphorane (2.83 g, 7.5 mmol) slowly and the reaction stirred for 1 hour at the same temperature under nitrogen. The reaction mixture was quenched with a saturated solution of $NH_4Cl$ (75 mL) and the compound was extracted into $CH_2Cl_2$ (75 mL). The organic layer was dried over $Na_2SO_4$, concentrated under reduced pressure, and purified on silica gel chromatography to give compound 3e (2.94 g, 61%); $^1H$ NMR (400 MHZ, $CDCl_3$) δ 7.44–7.26 (m, 10H), 6.98 (s, 1H), 6.6 (s, 1H), 5.5 (s, 1H), 4.59 (d, J=12.4 Hz, 1H), 4.38 (d, J=12.4 Hz, 1H), 4.19 (d, J=17.54 Hz, 1H), 3.8 (d, J=17.54 Hz, 1H), 1.5 (s, 9H).

c. Benzhydryl 7-[(Z)-(tert-butoxycarbonyl)methylene]-3'-chloro-3'-(desacetoxy)cephalosporinate (4e). To a solution of 3e (0.53 g, 1.04 mmol) in $CH_2Cl_2$ (10 mL) was added m-CPBA (70%) (0.56 g, 2.27 mmol) and phosphate 6.4 buffer (10 mL) and the reaction stirred for 1 hour. The reaction mixture was diluted with $CH_2Cl_2$ and the organic layer was washed with $Na_2SO_3$ (2×20 mL) followed by $NaHCO_3$ (2×25 mL) and the product was extracted into $CH_2Cl_2$ (20 mL), dried over sodium sulphate, concentrated under reduced pressure and purified by silica gel column chromatography to give 0.39 g (71%) of 4e. $^1H$ NMR (400 MHZ, $CDCl_3$) δ 7.44–7.25 (m, 10H), 6.98 (s, 1H), 6.59 (s, 1H), 5.53 (s, 1H), 4.58 (d, J=12.4 Hz, 1H), 4.37 (d, J=12.4 Hz, 1H), 4.14 (d, J=17.5 Hz, 1H), 3.82 (d, J=17.5 Hz, 1H), 1.5 (s, 9H).

d. Benzhydryl 7-[(Z)-(tert-Butylcarboxy)methylene]-3'-desacetoxy-3'-[1"-methyl-1"H-tetrazol-5"-yl)thio] cephalosporinate Sulfone (4f). To a solution of 5-mercapto-1-methyltetrazole (0.65 g, 1.02 mmol) in acetone (9 mL) and $H_2O$ (3 mL) was added $NaHCO_3$ (0.095 g, 1.13 mmol) followed by compound 4e. The reaction was stirred for 3 hours. The reaction mixture was then washed with water (10 mL) and the compound was extracted with $CH_2Cl_2$. The organic layer was dried over $Na_2SO_4$ and concentrated under reduced pressure to give 0.57 g (89%) of compound 4f; $^1H$ NMR (400 MHZ, $CDCl_3$) δ 7.47–7.26 (m, 10H), 6.94 (s, 1H), 6.56 (s, 1H), 4.66 (d, J=13.98 Hz, 1H), 4.44 (d, J=13.98 Hz, 1H), 4.11 (d, J=17.5 Hz, 1H), 4.01 (d, J=17.59 Hz, 1H), 3.87 (s, 3H), 1.51 (s, 9H).

e. Benzhydryl 7-[(Z)-(tert-Butylcarboxy)methylene]-3'-desacetoxy-2-exomethylidene-3'-[1"-methyl-1"H-tetrazol-5"-yl)thio]cephalosporinate Sulfone (5f). To a solution of sulfone 4f (0.25 g, 0.40 mmol) in dry $CH_3CN$ (10 mL) at 0° C. was added Eschenmoser's salt (0.223 g, 1.2 mmol) and the reaction was stirred at this temperature for 2 hours. $CH_3CN$ was then removed under reduced pressure. The residue was dissolved in $CH_2Cl_2$ (25 mL) and the solution washed with water (2×15mL). The organic layer was dried over $Na_2SO_4$ and concentrated to produce compound 5f (0.22 g. 88%); $^1H$ NMR (400 MHZ, $CDCl_3$) δ 7.43–7.26 (m, 10H), 6.99 (s, 1H), 6.80 (s, 1H), 6.67 (d, J=14 Hz, 2H), 5.69 (s, 1H), 4.72 (d, J=13.84 Hz, 1H), 4.34 (d, J=13.84 Hz, 1H), 4.11 (d, J=17.59 Hz, 1H), 3.83 (s, 3H), 1.51 (s, 9H).

Example 6

Sodium [2-1(Bisthiomethyl)exomethylene]-7-[(Z)-(2"-pyridinyl)methylene]-3'-desacetoxycephalosporinate (6 g)

To a solution of compound 5 g (0.2 g, 0.35 mmol) in anisole (1.16 mL) at 0° C. was added TFA (2.75 mL, 42 mmol) and the reaction stirred for 10 minutes. TFA and anisole were removed in vacuo. The residue was dissolved in EtOAc and the compound was extracted into an aqueous solution of $NaHCO_3$ [0.045 g/10 mL $H_2O$, 0.53 mmol]. The aqueous layer was loaded onto a column of the high porous polymer CHP20P (MitsubishI Chemical Corp., White Plains, N.Y.) and the compound was eluted in 5–10% $EtOH/H_2O$ to give compound 6 g; NMR (400 MHZ, $D_2O$) δ 8.51 (d, J=4 Hz, 1H), 7.80 (1H), 7.61 (d, J=7.8 Hz, 1H), 7.37 (m, 2H), 6.12 (s, 1H), 2.45 (s, 3H), 2.32 (s, 3H), 2.04 (s, 3H).

The intermediate compound 5 g was prepared as follows.

a. Benzhydryl 3'-Desacetoxy-2-[exo(bisthiomethyl) methylidene]-7-[(Z)(2"-pyridinyl)methylene] cephalosporinate Sulfone (5 g). To a solution of sulfone 4c (0.2 g, 0.41 mmol) in dry DMF (3 mL) at 0° C. was added NaH (60%, 0.032 g, 1.36 mmol) followed by $CS_2$ (0.197 mL, 3.28 mmol) and $CH_3I$ (0.077 mL, 1.22 mmol) and the reaction was stirred for 30 minutes. To the bright yellow reaction mixture was added crushed ice and the compound was extracted into toluene (15 mL). The toluene layer was dried, concentrated under pressure and purified on a silica gel column chromatography to produce compound 5 g (0.2 g, 87%); $^1H$ NMR (400 MHZ, $CDCl_3$) δ 8.71 (d, 1H), 7.72 (1H), 7.51 (2H), 7.39–7.23 (m, 11H), 6.95 (s, 1H), 5.68 (s, 1H), 4.15 (d, J=7.16 Hz, 1H), 4.11 (d, J=7.16 Hz, 1H), 2.52 (s, 3H), 2.49 (s, 3H), 2.38 (s, 3H).

Example 7

Disodium Salt of 7-[(Z)-(Carboxy)methylene]-2-(exomethylidene)-cephalosporinate Sulfone (6h)

To a solution of ester 5b (0.68 g, 1.16 mmol) in anisole (3.79 mL, 34.9 mmol) at 0° C. was added TFA (10.8 mL, 139 mmol) and the reaction mixture stirred for 10 minutes. TFA and anisole were removed in vacuo and the residue was dissolved in EtOAc and extracted into a solution of $NaHCO_3$ (0.146 g/10 mL $H_2O$). The aqueous layer was then loaded onto a column of the high porous polymer CHP20P (MitsubishI Chemical Corp., White Plains, N.Y.) and compound 6h was eluted with water; $^1H$ NMR (400 MHZ, $D_2O$) 6h δ 6.71 (s, 1H), 6.51 (s, 1H). 6.35 (s, 2H), 5.11 (d, J=11 Hz), 4.8 (d, J=11Hz, 1H), 2.04 (s, 3H), 1.46 (s, 9H).

Example 8

Disodium Salt 7-[(Z)(Carboxy)methylene]-3'-desacetoxy-2-(exo-methylidene)cephalosporinate Sulfone (6i)

To a solution of ester 5d (0.3 g, 0.572 mmol) in anisole (1.86 mL, 17.2 mmol) at 0° C. was added TFA (2.65 mL, 34.3 mmol) and the reaction stirred for 10 minutes. TFA and anisole were removed in vacuo and the residue was dissolved in EtOAc (10 mL). The compound was extracted into a solution of $NaHCO_3$ (0.072 g, 0.858 mmol). The aqueous layer was loaded onto a column of the high porous polymer CHP20P (MitsubishI Chemical Corp., White Plains, N.Y.) and elution with water gave the disalt 6i; $^1H$ NMR (400 MHZ, $D_2O$) δ 6.69 (s, 1H), 6.49 (s, 1H), 6.12 (s, 1H), 5.88 (s, 1H), 1.9 (s, 3H). $^1H$ NMR (400 MHZ, $D_2O$) 6d, δ 6.45 (s, 1H), 5.79 (s, 1H), 1.71 (s, 3H), 1.30 (s, 9H).

Examples 9–19

The following compounds were prepared as illustrated in FIGS. 3 and 4:

Benzhydryl 3-(acetoxymethyl)-7Z-[(2'-pyridyl) methylidene]-3-cephem-4-carboxylate (7) was prepared from 2 using a procedure similar to that described by J. D. Buynak et. al. *J. Med. Chem.* 38, 1022–1034, 1995.

Benzhydryl 3-(acetoxymethyl)-7Z-[(2'-pyridyl) methylidene]-2-cephem-4-carboxylate (8). A solution of 7 (7.0 g, 13.6 mmol) and $Et_3N$ (1.58 g, 15.6 mmol in $CHCl_3$ was heated at reflux for 4 hours under argon. The reaction mixture was concentrated in vacuo and the residue was purified by flash chromatography on silica (eluent: 5 to 15% EtOAc in hexane) to provide 3.88 g (55%) 8 and 1.3 g (18.5%) 7; $^1H$ NMR ($CDCl_3$): δ 1.94 (s, 3H), 4.65, 4.56 (ABq, J=25.5 Hz, 2H), 5.26 (s, 1H), 5.89 (s, 1H), 6.48 (s, 1H), 6.91 (s, 1H), 6.94 (s, 1H), 7.36–7.23 (m, 12H), 7.70 (t, J=2.2 Hz, 1H), 8.60 (d, J=4.2 Hz, 1H).

Benzhydryl 3-(hydroxymethyl)-7Z-[(2'-pyridyl) methylidene]-2-cephem-4-carboxylate (9). To a solution of 8 (1.1 g, 2.14 mmol) in $CH_2Cl_2$ (5 mL), was added $H_2O$ (0.1 mL) and then a second solution of p-toluenesulfonic acid (0.46 g, 2.46 mmol) in $CH_3OH$ (10 mL). The reaction was stirred for 24 to 30 hours. The solvent was removed in vacuo. The residue was dissolved in $CH_2Cl_2$ (20 mL), washed with saturated aqueous $NaHCO_3$, water and brine, and dried over $Na_2SO_4$. The solvent was removed in vacuo and the product purified by flash chromatography on silica (eluent: 25% EtOAc in hexane) to provide 525 mg (51%) 9; $^1H$ NMR ($CDCl_3$): δ 4.14, 4.09 (ABq, J=16.2 Hz, 2H), 5.32 (s, 1H), 5.70 (s, 1H), 5.90 (s, 1H), 6.92 (s, 1H), 6.94 (s, 1H), 7.35–7.21 (m, 12H), 7.69 (t, J=1.8 Hz, 1H), 8.60 (d, J=4.5 Hz, 1H).

Benzhydryl 3-formyl-7Z-[(2'-pyridyl)methylidene]-2-cephem-4-carboxylate (10). Celite (2 g) was added to a solution of 9 (3.2 g, 6.79 mmol) in anhydrous $CH_2Cl_2$ at 0° C. Pyridinium dichromate (2.93 g, 7.81 mmol) was then added in three equal portions over a 15 minute period. The reaction was allowed to stir at 0° C. for 2 hours. The reaction mixture was then filtered and the filtrate passed quickly through a small bed of silica gel and concentrated in vacuo to provide 2.6 g (81%) of 10; $^1H$ NMR ($CDCl_3$): δ 5.72 (s, 1H), 5.88 (s, 1H), 6.84 (s, 1H), 6.98 (s, 1H), 7.37–7.25 (m, 12H), 7.58 (s, 1H), 7.71 (t, J=2.2 Hz, 1H), 8.60 (d, J=3.9 Hz, 1H), 9.30 (s, 1H).

General Procedure for the preparation of Alkenes 11a, 11b, 11d, and 11e. A solution of aldehyde 10 (0.5 mmol) and the requisite ylide (5.0 mmol) was stirred in anhydrous THF (10 mL) at room temperature for approximately 24 hours. The solvent was removed in vacuo and the residue was purified by flash chromatography on silica using 5 to 20% EtOAc in hexane (in the case of compound 11d, 2% MeOH in $CH_2Cl_2$ was required).

Benzhydryl 3-[2'E-(cyanoethenyl)]-7Z-[(2"-pyridyl) methylidene]-2-cephem-4-carboxylate (11a). Using the general procedure described above, the title compound was prepared; yield: 82%; $^1H$ NMR ($CDCl_3$): δ 5.30–5.34 (m, 2H), 5.98 (s, 1H), 6.90–6.84 (m, 2H), 6.98 (s, 1H), 7.40–7.28 (m, 13H), 7.73 (t, J=1.6 Hz, 1H), 8.62 (d, J=3.78 Hz, 1H).

Benzhydryl 3-[2'E-(methoxyarbonylethenyl)]-7Z-[(2"-pyridyl)methylidene]-2-cephem-4-carboxylate (11b). Using the general procedure described above, the title compound was prepared; yield: 96%; $^1H$ NMR ($CDCl_3$): δ 3.67 (s, 3H), 5.38 (s, 1H), 5.85 (d, J=18.0 Hz, 1H), 5.91 (s, 1H), 6.78 (s, 1H), 6.82 (s, 1H), 6.90 (s, 1H), 7.10–7.28 (m, 13H), 7.60–7.64 (mn, 1H), 8.55 (d, J=4.0 Hz, 1H).

Benzhydryl 3-[2'E-(2"-pyridyl)ethenyl]-7Z-[(2'"-pyridyl)methylidene]-2-cephem-4-carboxylate (11c). To a slurry of triphenyl(2-pyridylmethyl)phosphonium chloride (0.39 g, 0.75 mmol) in anhydrous THF (20 mL) was added $NaNH_2$ (29 mg, 0.75 mmol) under argon and the reaction allowed to stir at room temperature for 2 hours. The reaction mixture allowed to settle for an additional 2 hours. The clear upper layer was carefully cannulated under argon into another flask containing a solution of the aldehyde 10 (235 mg, 0.5 mmol) in anhydrous $CH_2Cl_2$ (10 mL) at −78° C. The reaction was stirred for 1 hour at −78° C., and poured into a separatory funnel containing sat. aq. $NH_4Cl$. The organic layer was collected, dried on $Na_2SO_4$, and concentrated in vacuo. The residue was purified by flash chromatography on silica gel using 10 to 20% EtOAc in hexane to provide 0.21 g (78%) 11c; $^1$H NMR (CDCl$_3$): δ 5.29 (s, 1H), 5.62 (s, 1H), 5.99 (s, 1H), 6.64 (d, J=17.4 Hz, 1H), 6.66 (s, 1H), 6.92 (s, 1H), 6.95 (s, 1H), 7.21–7.33 (m, 14H), 7.62–7.63 (m, 1H), 7.69 (t, J=2.8 Hz, 1H), 8.54 (d, J=4.52 Hz, 1H), 8.60 (d, J=3.84 Hz, 1H).

Benzhydryl 3-[prop-1'E-ene-3'-amide)]-7Z-[(2"-pyridyl)methylidene]-2-cephem-4-carboxylate (11d). Using a procedure similar to that described by S. Trippet, and D. M. Walker, *J. Chem. Soc.* 3874, 1959, the requisite ylide (carbamoylmethylenetriphenyl-phosphorane) was obtained as follows: A solution of carbamoylmethyltriphenyl-phosphonium chloride (5 g, 14.0 mmol), (itself obtained from chloroacetamide and triphenylphosphine in refluxing nitromethane) in $H_2O$ (75 mL) was cooled to 0° C. and a cold (0–5° C.) solution of NaOH (0.56 g in 5 mL $H_2O$) was added in one portion. The resultant mixture was immediately filtered and washed with cold water (75 mL). The collected precipitate was dried under high vacuum to provide carbamoylmethylenetriphenylphosphorane. This ylide was reacted with aldehyde 10 according to the general procedure above to give the title compound; yield: 78%; $^1$H NMR (CDCl$_3$): δ 5.41 (s, 1H), 5.70 (d, J=15.5 Hz, 1H), 5.95 (s, 1H), 6.84 (s, 1H), 6.87 (s, 1H), 6.96 (s, 1H), 7.23–7.36 (m, 13H), 7.69–7.72 (m, 2H), 8.60 (d, J=4.12 Hz, 1H).

Benzhydryl 3-[2'E-(tert-butoxycarbonyl)ethenyl]-7Z-[(2"-pyridyl)methylidene]-3-cephem-4-carboxylate (11e). Using the general procedure described above, the title compound was prepared; $^1$H NMR (CDCl$_3$).: δ 1.48 (s, 9H), 5.44 (s, 1H), 5.92 (d, J=15.8 Hz, 1H), 5.96 (s, 1H), 6.78 (s, 1H), 6.87 (s, 1H), 6.94 (s, 1H), 7.13 (d, J=15.8 Hz, 1H), 7.23–7.34 (m, 12H), 7.70 (t, J=7.7 Hz, 1H), 8.60 (d, J=4.12 Hz, 1H).

Benzhydryl 3-[2'Z-chloro-2'-(methoxycarbonyl)ethenyl]-7Z-[1 (2"-pyridyl)methylidene]-2-cephem-4-carboxylate (11f). A solution of methyl (triphenylphosphoranylidene)acetate (0.267 g, 0.79 mmol) in anhydrous THF was chilled to −20° C. and N-chlorosuccinimide (0.1 g, 0.79 mmol) and NaHCO$_3$ (0.1 g, 7.5 mmol) was added. After stirring for 30 minutes at −20° C., aldehyde 10 (75 mg, 0.15 mmol) was added. The reaction was allowed to come to room temperature and was stirred for 36 hours. The solvent was removed in vacuo and the residue was purified by flash chromatography on silica to provide 73 mg (82%) 11f; $^1$H NMR (CDCl$_3$): δ 3.72 (s, 3H), 5.44 (s, 1H), 5.96 (s, 1H), 6.84 (s, 1H), 6.87 (s, 1H), 6.95 (s, 1H), 7.27–7.69 (m, 13H), 7.69 (t, J=7.34 Hz, 1H), 8.60 (d, J=3.58, 1H).

Benzhydryl 3-[2'E-nitroethenyl]-7Z-[(2'"-pyridyl)methylidene]-2-cephem-4-carboxylate (11h). A solution of aldehyde 10 (50 mg, 0.107 mmol), AcOH (63 mg, 1.07 mmol), and NH$_4$OAc (41 mg, 0.533 mmol) in CH$_3$NO$_2$ (2 mL) was heated at 50° C. for 2 hours. The reaction was monitored by tlc, and if it was not complete, an additional quantity of NH$_4$OAc (20 mg, 0.26 mmol) was added and stirring was continued for an additional 1 hour. Volatiles were removed in vacuo and the residue was redissolved in CH$_2$Cl$_2$ (20 mL). The resultant solution was washed with water, brine, and dried over Na$_2$SO$_4$. Concentration in vacuo and purification by flash chromatography on silica gel provided 48 mg (92%) 11h as a yellow solid; $^1$H NMR (CDCl$_3$): δ 5.33 (s, 1H), 6.02 (s, 1H), 6.91 (s, 1H), 7.00 (s, 1H), 7.13 (s, 1H), 7.23 (d, J=13.8 Hz, 1H), 7.27–7.36 (m, 12H), 7.50 (d, J=13.8 Hz 1H), 7.73 (t, J=7.24 Hz, 1H), 8.62 (d, J=4.22 Hz, 1H).

Benzhydryl 3-(E-oximinomethyl)-7Z-[(2'-pyridyl)methylidene]-2-cephem-4-carboxylate (14). A solution of aldehyde 10 (0.1 g, 0.21 mmol) and hydroxylamine hydrochloride (0.03 g, 0.42 mmol) in anhydrous isopropanol (4 mL) was heated at 80° C. for 3 hours. The solvent was then removed in vacuo and the residue dissolved in CH$_2$Cl$_2$ (20 mL). This solution was washed with 10% NaHCO$_3$, water, and brine and dried over Na$_2$SO$_4$. Removal of the volatiles provided the oxime 14 (92 mg, 90%); $^1$H NMR (CDCl$_3$): δ 5.61 (s, 1H), 5.78 (s, 1H), 6.64 (s, 1H), 6.88 (s, 1H), 6.95 (s, 1H), 7.22–7.38 (m, 12H), 7.65–7.68 (m, 2H), 8.60 (d, J=4.38 Hz, 1H).

Benzhydryl 3-cyano-7Z-[(2'-pyridyl)methylidene]-2-cephem-4-carboxylate (17). To a solution of oxime 14 (0.1 g, 0.2 mmol) in anhydrous CHCl$_3$ (5 mL) was added SOCl$_2$ (25 mg, 0.2 mmol) by syringe and the reaction mixture was heated to reflux for 30 minutes. The solution was cooled, washed with 5% aq NaHCO$_3$, water, and brine, and dried over Na$_2$SO$_4$. Purification by flash chromatography on silica gel provided the nitrile 17 (78 mg, 82%); $^1$H NMR (CDCl$_3$): δ 5.30 (s, 1H), 5.48 (s, 1H), 5.89 (s, 1H), 6.92 (s, 1H), 6.99 (s, 1H), 7.21–7.47 (m, 12H), 7.71 (t, J=7.41 Hz, 1H), 8.57 (d, J=4.4 Hz, 1H).

General Procedure for Formation of Sulfones 12a, 12b, 12c, 12d, 12e, 12f, 12h, 15, and 18. To a biphasic mixture of CH$_2$Cl$_2$ (20 mL) and buffer (pH=6.4, phosphate buffer, Aldrich Chemical Co., 10 mL), was added the requisite sulfide prepared above, (0.2 mmol) and MCPBA (1.0 mmol) at room temperature. The reaction was stirred for 30 minutes. The organic layer was separated and washed with saturated aqueous NaHSO$_3$, saturated aqueous NaHCO$_3$, water, and brine. Removal of the solvent in vacuo provided the sulfone 12 (quantitative yield).

Benzhydryl 3-[2'E-(cyanoethenyl)]-1,1-dioxo-7Z-[(2"-pyridyl)methylidene]-3-cephem-4-carboxylate (12a). Using the general procedure described above, the title compound was prepared; $^1$H NMR (CDCl$_3$): δ 3.81 (d, J=17 Hz, 1H), 4.04 (d, J=17 Hz, 1H), 5.34 (d, J=16.5 Hz, 1H), 6.05 (s, 1H), 7.12 (s, 1H), 7.35–7.55 (m, 14H), 7.78 (s, 1H), 8.72 (s, 1H).

Benzhydryl 1,1-dioxo-3-[2'E-(methoxycarbonylethenyl)]-7Z-[(2"-pyridyl)methylidene]-3-cephem-4-carboxylate (12b). Using the general procedure described above, the title compound was prepared; $^1$H NMR (CDCl$_3$): δ 3.68 (s, 3H), 3.78 (d, J=17.2 Hz, 1H), 4.02 (d, J=17.2 Hz, 1H), 5.86–5.92 (m, 2H), 7.01 (s, 1H), 7.25–7.36 (m, 12H), 7.44 (d, 1H, J=4.22H, 7.66–7.70 (m, 1H), 7.87 (d, J=15.9 Hz, 1H), 8.63 (d, J=4.27 Hz 1H).

Benzhydryl 1,1-dioxo-3-{2'E-[2"-(pyridin-N-oxide)ethenyl]}-7Z-[(2'"-pyridyl)methylidene]-3-cephem-4-carboxylate (12c). Using the general procedure described above, the title compound was prepared; $^1$H NMR (CDCl$_3$): δ 4.12 (d, J=17.1 Hz, 1H), 4.35 (d, J=17.1 Hz, 1H), 5.27 (s, 1H), 7.03 (s, 1H), 7.26–7.69 (m, 18H), 8.17 (s, 1H), 8.66 (s, 1H).

Benzhydryl 1,1-dioxo-3-[prop-1'E-ene-3'-amide)]-7Z-[(2"-pyridyl)methylidene]-3-cephem-4-carboxylate (12d). Using the general procedure described above, the title compound was prepared; $^1$H NMR (CDCl$_3$): δ 3.87 (d, J=17.1 Hz, 1H), 4.07 (d, J=17.1 Hz, 1H), 5.44 (brs, 2H), 5.94–5.98 (m, 2H), 7.05 (s, 1H), 7.25–7.68 (m, 10H), 7.51–7.56 (m, 2H), 7.64–7.74 (m, 2H), 7.80 (d, J=15.8 Hz, 1H), 8.68 (d, J=4.32 Hz, 1H).

Benzhydryl 3-[2'E-(tert-butoxycarbonyl)ethenyl]-1,1-dioxo-7Z-[(2"-pyridyl)methylidene]-3-cephem-4-carboxylate (12e). Using the general procedure described above, the title compound was prepared; $^1$H NMR (CDCl$_3$): δ 1.46 (s, 9H), 3.78 (d, ABq, J=20.5 Hz, 1H), 4.06 (d, ABq, J=20.5 Hz, 1H), 5.88 (d, J=18.1 Hz, 1H), 5.95 (s, 1H), 6.04 (s, 1H), 6.22 (d, J=18.1 Hz, 1H), 6.88 (s, 1H), 7.04 (s, 1H), 7.24–7.52 (m, 12H), 7.73–7.75 (m, 1H), 8.68 (s, 1H).

Benzhydryl 1,1-dioxo-3-[2'Z-chloro-2'-(methoxycarbonyl)ethenyl]-7Z-[(2"-pyridyl)methylidene]-3-cephem-4-carboxylate (12f). Using the general procedure described above, the title compound was prepared; $^1$H NMR (CDCl$_3$): δ 3.73 (s, 3H), 3.87 (d, J=17.2 Hz, 1H), 4.02 (d, J=17.2 Hz, 1H), 5.91 (s, 1H), 5.95 (s, 1H), 5.98 (s, 1H), 7.06 (s, 1H), 7.29–7.39 (m, 12H), 7.89–7.93 (m, 1H), 8.66 (d, J=4.24 Hz, 1H).

Benzhydryl 1,1-dioxo-3-[2'E-nitroethenyl]-7Z-[(2"-pyridyl)methylidene]-3-cephem-4-carboxylate (12h). Using the general procedure described above, the title compound was prepared; $^1$H NMR (CDCl$_3$): δ 3.94 (d, J=18.1 Hz, 1H), 4.12 (d, J=18.1 Hz, 1H), 5.98 (s, 1H), 6.96 (s, 1H), 7.04 (d, J=14.6 Hz, 1H), 7.12 (s, 1H), 7.26–7.38 (m, 12H), 7.54 (d, J=14.6 Hz, 1H), 7.74 (t, J=7.86 Hz, 1H), 8.61 (d, J=4.22 Hz, 1H).

Benzhydryl 3-[2'E-(tert-butoxycarbonyl)ethenyl]-1,1-dioxo-2-methylidene-7Z-[(2"-pyridyl)methylidene]-3-cephem-4-carboxylate (20). To a solution of sulfone 12e (0.1 mmol) in anh CH$_3$CN (10 mL), Eschenmoser's salt (0.4 mmol) was added at room temperature. The reaction was stirred under argon for 3 hours. CH$_3$CN was removed under reduced pressure and the residue dissolved in CH$_2$Cl$_2$ (15 mL). The CH$_2$Cl$_2$ layer was then washed with water and brine, and dried over Na$_2$SO$_4$. Purification by flash chromatography on silica gel using 5% EtOAc/CH$_2$Cl$_2$ provided 20 (90% yield); $^1$H NMR (CDCl$_3$): δ 1.38 (s, 9H), 5.95 (d, J=16.0 Hz, 1H), 6.01 (s, 1H), 6.14 (s, 1H), 6.70 (s, 1H), 6.94 (s, 1H), 7.25–7.40 (m, 14H), 7.82 (t, J=6.68 Hz, 1H), 8.61 (d, J=3.84 Hz, 1H).

Benzhydryl 1,1-dioxo-3-(E-oximinomethyl)-7Z-[(2'-pyridyl)methylidene]-3-cephem-4-carboxylate (15). Using the general procedure described above, the title compound was prepared; $^1$H NMR (CDCl$_3$): δ 4.08 (d, J=17.4 Hz, 1H), 4.30 (d, J=17.4 Hz, 1H), 5.88 (s, 1H), 6.99 (s, 1H), 7.12–7.24 (m, 13H), 7.42–7.52 (m, 2H), 8.62 (d, J=3.9 Hz, 1H).

Benzhydryl 1,1-dioxo-3-cyano-7Z-[(2'-pyridyl)methylidene]-3-cephem-4-carboxylate (18). Using the general procedure described above, the title compound was prepared; $^1$H NMR (CDCl$_3$): δ 3.82 (d, J=18.2 Hz, 1H), 4.12 (d, J=18.2 Hz, 1H), 5.47 (s, 1H), 6.02 (s. 1H), 7.04 (s. 1H), 7.21–7.46 (m, 12H), 7.72 (t, J=8.2 Hz, 1H), 8.66 (d, J=4.52 Hz, 1H).

General Procedure for Conversion of Benzhydryl Esters (12a, 12b, 12c, 12d, 12e, 12f, 12h, 15, 18 and 20) to the Corresponding Sodium Carboxylates (13a, 13b, 13c, 13d, 13e, 13f, 13 g, 13h, 16, 19, and 21). A solution of the benzhydryl ester (0.1 mmol) in anisole (3.0 mmol) was cooled in an ice-salt bath and TFA (12.0 mmol) was slowly added via syringe under argon. After 20 minutes, the volatiles were removed in vacuo and the residue was dissolved in EtOAc (5 mL). The EtOAc layer was extracted with aqueous NaHCO$_3$ (2×0.15 mmol in 4 mL H$_2$O). The combined NaHCO$_3$ layers were directly loaded on a column (high porous polymer, MCI gel, CHP20P, Mitsubishi Chemical Corp., White Plains, N.Y., approx. 75 to 150 mL of resin) and the product eluted with 5% EtOH in deionized (millipore) water. Yields were between 60 to 80%.

Example 9

Sodium 3-[2'E-(Cyanoethenyl)]-1,1-dioxo-7Z-[(2"-pyridyl)methylidene]-3-cephem-4-carboxylate (13a)

$^1$H NMR (D$_2$O): δ 5.55 (d, J=16.4 Hz, 1H), 6.40 (s, 1H), (7.46, t, J=5.12 Hz, 1H), 7.50 (d, J=16.4 Hz, 1H), 7.59 (s, 1H), 7.68 (d, J=7.76 Hz, 1H), 7.89 (t, J=7.62 Hz, 1H), 8.62 (d, J=4.54 Hz, 1H).

Example 10

Sodium 1,1-Dioxo-3-[2'E-(methoxycarbonylethenyl)]-7Z-[(2"-pyridyl)methylidene]-3-cephem-4-carboxylate (13b)

$^1$H NMR (D$_2$O): δ 3.72 (s, 3H), 5.70 (d, J=22.0 Hz, 1H), 7.46–7.43 (m, 2H), 7.53 (s, 1H), 7.68–7.62 (m, 2H), 7.88 (t, J=6.70 Hz, 1H), 8.60 (d, J=4.1 Hz, 1H).

Example 11

Sodium 1,1-Dioxo-3-{2'E-[2"-(pyridin-N-oxide)ethenyl]}-7Z-[(2'''-pyridyl)methylidene]-3-cephem-4-carboxylate (13c)

$^1$H NMR (D$_2$O): δ 6.04 (s, 1H), 7.03 (d, J=16.5 Hz, 1H), 7.39 (t, J=6.9 Hz, 1H), 7.45 (t, J=4.96 Hz, 1H), 7.52–7.62 (m, 4H), 7.80 (d, J=8.1 Hz, 1H), 7.88 (t, J=7.75 Hz, 1H), 8.23 (d, J=6.46 Hz, 1H), 8.62 (d, J=4.38 Hz).

Example 12

Sodium 1,1-Dioxo-3-[prop-1'E-ene-3'-amide)]-7Z-[(2"-pyridyl)methylidene]-3-cephem-4-carboxylate (13d)

$^1$H NMR (D$_2$O): δ 6.04 (d, J=15.6 Hz, 1H), 6.38 (s, 1H), 7.47–7.57 (m, 3H), 7.68 (d, J=7.6 Hz, 1H), 7.89 (brs, 1H), 8.61 (s, 1H).

Example 13

Sodium 1,1-Dioxo-3-[2'E-(t-butoxycarbonylethenyl)]-7Z-[(2"-pyridyl)methylidene]-3-cephem-4-carboxylate (13e)

$^1$H NMR (D$_2$O): δ 1.45 (s, 9H), 5.88 (d, J=15.8 Hz, 1H), 6,39 (s, 1H), 7.46 (t, J=5.09 Hz, 1H), 7.55–7.61 (m, 2H), 7.69 (d, J=11.8 Hz, 1H), 7.90(t, J=8.11 Hz, 1H), 8.62 (d, J=4.73 Hz, 1H).

Example 14

Sodium 1,1-Dioxo-3-[2'Z-chloro-2'-(methoxycarbonyl)ethenyl]-7Z-[(2"-pyridyl)methylidene]-3-cephem-4-carboxylate (13f)

1H NMR (D$_2$O): δ 3.81 (s, 3H), 6.0 (d, J=15.8 Hz, 1H), 6.46 (s, 1H), 7.53 (t, J=7.52 Hz, 1H), 7.64 (s, 1H), 7.74–7.71 (m, 1H), 7.95 (t, J=7.77 Hz, 1H), 8.68 (d, J=4.52 Hz, 1H).

Example 15

Disodium 3-[2'E-Carboxyethenyl]-1,1-dioxo-7Z-[(2"-pyridyl)methylidene]-3-cephem-4-carboxylate (13 g)

Hydrolysis of compound 12e under the above general conditions gave a mixture of compound 13e and the title compound 13 g, which was separated by chromatography to give the title compound; $^1$H NMR (D$_2$O): δ 5.92 (d, J=15.8 Hz, 1H), 6.36 (s, 1H), 7.34 (d, J=15.8 Hz, 1H), 7.45–7.48 (m, 1H), 7.55 (s, 1H), 7.69 (d, J=7.8 Hz, 1H), 7.92 (t, J=7.8 Hz. 1H), 8.63 (d, J=3.6 Hz, 1H).

Example 16

Sodium 1,1-Dioxo-3-[2'E-nitroethenyl]-7Z-[(2"-pyridyl)methylidene]-3-cephem-4-carboxylate (13h)

$^1$H NMR (D$_2$O): δ 6.02 (s, 1H), 7.11 (s, 1H), 7.16 (d, J=15.6 Hz, 1H), 7.20–7.22 (m, 2H), 7.28 (d, J=15.6 Hz, 1H), 7.78 (t, J=6.2 Hz, 1H), 8.62 (d, J=2.88 Hz, 1H).

Example 17

Sodium 1,1-Dioxo-3-(E-oximinomethyl)-7Z-[(2'-pyridyl)methylidene]-3-cephem-4-carboxylate (16)

$^1$H NMR (D$_2$O): δ 6.31 (s, 1H), 7.39 (t, J=7.84 Hz, 1H), 7.48 (d, J=7.78 Hz, 1H). 7.71–7.74 (m, 2H), 8.35 (s, 1H), 8.36 (d, J=6.34 Hz, 1H).

Example 18

Sodium 1,1-Dioxo-3-cyano-7Z-[(2'-pyridyl)methylidene]-3-cephem-4-carboxylate (19)

$^1$H NMR (D$_2$O): δ 6.40 (s, 1H), 7.49–7.52 (m, 1H), 7.61 (s, 1H), 7.69–7.74 (m, 1H), 7.93–7.91 (m, 1H), 8.63 (d, J=4.6 Hz, 1H).

Example 19

Disodium 3-[2'E-Carboxyethenyl]-1,1-dioxo-2-methylidene-7Z-[(2"-pyridyl)methylidene]-3-cephem-4-carboxylate (21)

$^1$H NMR (D$_2$O): δ 5.80 (m, 2H), 6.02 (s, 1H), 6.23 (d, J=18.4 Hz, 1H), 7.12 (d, J=18.4 Hz, 1H), 7.21 (s, 1H), 7.26–7.31 (m, 2H), 7.79 (t, J=7.8 Hz, 1H), 8.51 (d, J=4.4 Hz, 1H).

Example 20

The following illustrate representative pharmaceutical dosage forms, containing a compound of formula I or IV ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0–7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (vii) Tablet 1 | mg/tablet |
|---|---|
| 'Compound X' | 100.0 |
| β-lactam antibiotic | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 400.0 |

| (viii) Tablet 2 | mg/tablet |
|---|---|
| 'Compound X' | 20.0 |
| β-lactam antibiotic | 20.0 |
| Microcrystalline cellulose | 410.0 |
| Starch | 50.0 |
| Sodium starch glycolate | 15.0 |
| Magnesium stearate | 5.0 |
| | 520.0 |

| (ix) Capsule | mg/capsule |
|---|---|
| 'Compound X' | 10.0 |
| β-lactam antibiotic | 10.0 |
| Colloidal silicon dioxide | 1.5 |
| Lactose | 465.5 |
| Pregelatinized starch | 120.0 |
| Magnesium stearate | 3.0 |
| | 610.0 |

| (x) Injection 1 | mg/mL |
|---|---|
| 'Compound X' (free acid form) | 1.0 |
| β-lactam antibiotic | 2.0 |
| Dibasic sodium phosphate | 12.0 |
| Monobasic sodium phosphate | 0.7 |
| Sodium chloride | 4.5 |

-continued

| | |
|---|---|
| 1.0N Sodium hydroxide solution (pH adjustment to 7.0–7.5) | q.s. |
| Water for injection | q.s. ad 1 mL |

| (xi) Injection 2 | mg/mL |
|---|---|
| 'Compound X' (free acid form) | 10.0 |
| β-lactam antibiotic | 5.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0–7.5) | q.s. |
| Water for injection | q.s. ad 1 mL |

| (xii) Aerosol | mg/can |
|---|---|
| 'Compound X' | 20.0 |
| β-lactam antibiotic | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art. "β-lactam antibiotic" can be any compound possessing antibiotic properties (e.g. amoxicillin, piperacillin, ampicillin, ceftizoxime, cefotaxime, cefuroxime, cephalexin, cefaclor, cephaloridine, or ceftazidime). Although specific quantities of "Compound X" and "β-lactam antibiotic" are shown in the above illustrative examples, it is to be understood that the compounds can be present in any ratio provided the final formulation possesses the desired antibiotic properties.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

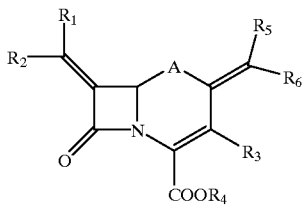

(I)

wherein:
$R_1$, $R_2$, $R_5$, and $R_6$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —COOR$_a$, —C(=O)NR$_b$R$_c$, —OC(=O)NR$_b$R$_c$, NR$_b$R$_c$, or —S(O)$_n$R$_d$; or $R_1$ and $R_2$ together with the carbon to which they are attached are $(C_3-C_8)$cycloalkyl or a heterocycle, wherein each $(C_3-C_8)$cycloalkyl or heterocycle is optionally substituted with $(C_1-C_{10})$alkyl, hydroxy, halo, $(C_1-C_{10})$alkoxy, $(C_1-C_{10})$alkanoyloxy, or $(C_1-C_{10})$alkoxycarbonyl; or $R_5$ and $R_6$ together with the carbon to which they are attached are $(C_3-C_8)$cycloalkyl or a heterocycle, wherein each $(C_3-C_8)$cycloalkyl or heterocycle is optionally substituted with $(C_1-C_{10})$alkyl, hydroxy, halo, $(C_1-C_{10})$alkoxy, $(C_1-C_{10})$alkanoyloxy, or $(C_1-C_{10})$alkoxycarbonyl;

$R_3$ is hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, halo, cyano, nitro, aryl, heterocycle, —COOR$_a$, —C(=O)NR$_b$R$_c$, —OC(=O)NR$_b$R$_c$, NR$_b$R$_c$, or —S(O)$_n$R$_d$;

$R_4$ is hydrogen;

A is thio, sulfinyl, or sulfonyl;

each n is independently 0, 1, or 2;

each $R_a$ is independently hydrogen, or $(C_1-C_{10})$alkyl;

each $R_b$ and $R_c$ is independently hydrogen, $(C_1-C_{10})$alkyl, $(C_1-C_{10})$alkoxy, phenyl, benzyl, phenethyl, or $(C_1-C_{10})$alkanoyl;

each $R_d$ is independently $(C_1-C_{10})$alkyl, $(C_1-C_{10})$alkanoyl, aryl, heterocycle, aryl$(C_1-C_6)$alkyl, heterocycle, or heterocycle$(C_1-C_6)$alkyl;

wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, or $(C_1-C_{10})$alkoxycarbonyl of $R_1$, $R_2$, $R_3$, $R_5$, and $R_6$ is optionally substituted with one or more substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$alkanoyloxy, aryloxy, (heterocycle)oxy, —COOR$_a$, $(C_3-C_8)$cycloalkyl, —C(=O)NR$_b$R$_c$, —OC(=O)NR$_b$R$_c$, NR$_b$R$_c$, and —S(O)$_n$R$_d$; and wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —COOR$_a$, —C(=O)NR$_b$R$_c$, —OC(=O)NR$_b$R$_c$, NR$_b$R$_c$, and —S(O)$_n$R$_d$;

or a pharmaceutically acceptable salt thereof.

2. The compound of claim 1 wherein $R_1$ is aryl, heterocycle, or —COOR$_a$.

3. The compound of claim 1 wherein $R_1$ is 2-pyridyl, or —COOR$_a$.

4. The compound of claim 1 wherein $R_2$ is hydrogen.

5. The compound of claim 1 wherein $R_3$ is hydrogen, carboxy, or —CH$_2$M; wherein M is hydrogen, halo, $(C_1-C_{10})$alkanoyloxy, or heterocycle.

6. The compound of claim 1 wherein $R_3$ is acetoxymethyl, phenylacetoxymethyl, (3,4-dihydroxyphenyl)acetoxymethyl, chloromethyl, formyl, or chloroacetoxymethyl.

7. The compound of claim 1 wherein $R_3$ is hydrogen, methyl, acetoxymethyl, or 1-methyl-1H-tetrazol-5-ylthiomethyl.

8. The compound of claim 1 wherein $R_3$ is vinyl, optionally substituted at the 2-position with halo, cyano, —COOR$_a$, trifluloromethyl, formyl, $(C_3-C_8)$cycloalkyl, $(C_2-C_{10})$alkenyl, $(C_2-C_{10})$alkynyl, heterocycle, or NR$_b$R$_c$.

9. The compound of claim 1 wherein $R_3$ is vinyl, optionally substituted at the 2-position with cyano, —COOR$_a$, $(C_2-C_{10})$alkenyl, or heteroaryl.

10. The compound of claim 1 wherein $R_3$ is 2-cyanovinyl, 2-(methoxycarbonyl)-vinyl, 2-(2-pyridyl-N-oxide)vinyl, or 1,3-butadienyl.

11. The compound of claim 1 which is a pharmaceutically acceptable salt of an acid of formula 1 wherein $R_4$ is hydrogen.

12. The compound of claim 1 wherein $R_5$ and $R_6$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —$COOR_a$, —$C(=O)NR_bR_c$, —$OC(=O)NR_bR_c$, $NR_bR_c$, or —$S(O)_nR_d$.

13. The compound of claim 1 wherein $R_5$ and $R_6$ together with the carbon to which they are attached are $(C_3-C_8)$cycloalkyl or a heterocycle, optionally substituted with $(C_1-C_{10})$alkyl, hydroxy, halo, $(C_1-C_{10})$alkoxy, $(C_1-C_{10})$alkanoyloxy, or $(C_1-C_{10})$alkoxycarbonyl.

14. The compound of claim 1 wherein $R_5$ and $R_6$ are each independently hydrogen, $(C_1-C_{10})$alkyl, $(C_3-C_8)$cycloalkyl, halo, —$COOR_a$ or —$S(O)_nR_d$; or $R_5$ and $R_6$ together with the carbon to which they are attached are a 5, 6, or 7 membered heterocycle comprising carbon and 1 or 2 N, O, or S.

15. The compound of claim 1 wherein $R_5$ and $R_6$ are each individually hydrogen.

16. The compound of claim 1 wherein $R_5$ and $R_6$ are each individually methylthio.

17. The compound of claim 1 wherein A is sulfonyl.

18. The compound of claim 1 wherein A is sulfonyl; $R_1$ is 2-pyridiyl, carboxy or tert-butoxy carbonyl; $R_2$ is hydrogen; $R_3$ is hydrogen, methyl, acetoxymethyl or 1-methyl-1H-tetrazol-5-ylthiomethyl; and $R_5$ and $R_6$ are the same and are each hydrogen or thiomethyl.

19. A pharmaceutical composition comprising a compound of formula I:

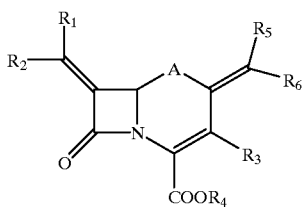

(I)

wherein:
$R_1$, $R_2$, $R_5$, and $R_6$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —$COOR_a$, —$C(=O)NR_bR_c$, —$OC(=O)NR_bR_c$, $NR_bR_c$, or —$S(O)_nR_d$; or $R_1$ and $R_2$ together with the carbon to which they are attached are $(C_3-C_8)$cycloalkyl or a heterocycle, wherein each $(C_3-C_8)$cycloalkyl or heterocycle is optionally substituted with $(C_1-C_{10})$alkyl, hydroxy, halo, $(C_1-C_{10})$alkoxy, $(C_1-C_{10})$alkanoyloxy, or $(C_1-C_{10})$alkoxycarbonyl; or $R_5$ and $R_6$ together with the carbon to which they are attached are $(C_3-C_8)$cycloalkyl or a heterocycle, wherein each $(C_3-C_8)$cycloalkyl or heterocycle is optionally substituted with $(C_1-C_{10})$alkyl, hydroxy, halo, $(C_1-C_{10})$alkoxy, $(C_1-C_{10})$alkanoyloxy, or $(C_1-C_{10})$alkoxycarbonyl;

$R_3$ is hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, halo, cyano, nitro, aryl, heterocycle, —$COOR_a$, —$C(=O)NR_bR_c$, —$C(=O)NR_bR_c$, $NR_bR_c$, or —$S(O)_nR_d$;

$R_4$ is hydrogen;

A is thio, sulfinyl, or sulfonyl;
   each n is independently 0, 1, or 2;
   each $R_a$ is independently hydrogen, or $(C_1-C_{10})$alkyl;
   each $R_b$ and $R_c$ is independently hydrogen, $(C_1-C_6)$alkyl, $(C_1-C_{10})$alkoxy, phenyl, benzyl, phenethyl, or $(C_1-C_{10})$alkanoyl;
   each $R_d$ is independently $(C_1-C_{10})$alkyl, $(C_1-C_{10})$alkanoyl, aryl, heterocycle, aryl$(C_1-C_6)$alkyl, heterocycle, or heterocycle$(C_1-C_6)$alkyl;
      wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, or $(C_1-C_{10})$alkoxycarbonyl of $R_1$, $R_2$, $R_3$, $R_5$, and $R_6$ is optionally substituted with one or more substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$alkanoyloxy, aryloxy, (heterocycle)oxy, —$COOR_a$, $(C_3-C_8)$cycloalkyl, —$C(=O)NR_bR_c$, —$OC(=O)NR_bR_c$, $NR_bR_c$, and —$S(O)_nR_d$; and
      wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —$COOR_a$, —$C(=O)NR_bR_c$, —$OC(=O)NR_bR_c$, $NR_bR_c$, and —$S(O)_nR_d$;

or a pharmaceutically acceptable salt thereof; and a pharmaceutically acceptable carrier.

20. A method comprising inhibiting a β-lactamase by contacting said β-lactamase with an effective amount of a compound of formula IV:

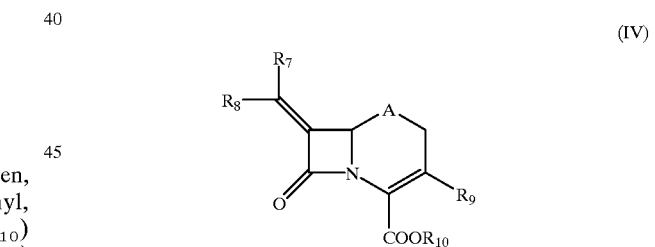

(IV)

wherein:
$R_7$ and $R_8$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —$COOR_e$, —$C(=O)NR_fR_g$, —$OC(=O)NR_fR_g$, $NR_fR_g$, or —$S(O)_nR_h$;

$R_9$ is cyano, —$CH=NOR_i$, or a radical of the following formula

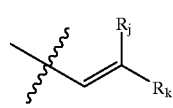

$R_{10}$ is hydrogen;

A is thio, sulfinyl, or sulfonyl;
each n is independently 0, 1, or 2;
each $R_e$ is independently hydrogen, or $(C_1-C_{10})$alkyl;
each $R_f$ and $R_g$ is independently hydrogen, $(C_1-C_{10})$alkyl, $(C_1-C_{10})$alkoxy, phenyl, benzyl, phenethyl, or $(C_1-C_{10})$alkanoyl;
each $R_h$ is independently $(C_1-C_{10})$alkyl, phenyl, aryl $(C_1-C_6)$alkyl, heterocycle, or heterocycle$(C_1-C_6)$alkyl;
$R_i$ is hydrogen or $(C_1-C_6)$alkyl; and
$R_j$ and $R_k$ are each independently hydrogen, halo, cyano, nitro, aryl, heterocycle, $(C_2-C_6)$alkenyl, —COOR$_e$, —C(=O)NR$_f$R$_g$, —OC(=O)NR$_f$R$_g$, NR$_f$R$_g$, or —S(O)$_n$R$_h$;
wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, or $(C_1-C_{10})$alkoxycarbonyl of $R_7$, $R_8$, $R_j$ and $R_k$ is optionally substituted with one or more [(e.g. 1, 2, 3, or 4)] substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$alkanoyloxy, aryloxy, (heterocycle)oxy, $(C_3-C_8)$cycloalkyl, —COOR$_e$, —C(=O)NR$_f$R$_g$, —OC(=O)NR$_f$R$_g$, NR$_h$R$_i$, or —S(O)$_n$R$_k$; and
wherein any aryl is optionally substituted with one or more [(e.g. 1, 2, 3, or 4)] substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —COOR$_e$, —C(=O)NR$_f$R$_g$, —OC(=O)NR$_f$R$_g$, NR$_h$R$_i$, or —S(O)$_n$R$_k$;

or a pharmaceutically acceptable salt thereof.

21. A therapeutic method comprising inhibiting a β-lactamase in a mammal in need of such therapy, by administering an effective inhibitory amount of a compound of formula IV:

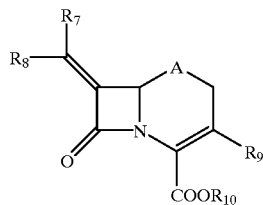

(IV)

wherein:

$R_7$ and $R_8$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$;

$R_9$ is cyano, —CH=NOR$_i$, or a radical of the following formula

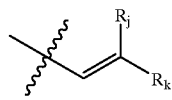

$R_{10}$ is hydrogen;
A is thio, sulfinyl, or sulfonyl;
each n is independently 0, 1, or 2;
each $R_e$ is independently hydrogen, or $(C_1-C_{10})$alkyl;
each $R_f$ and $R_g$ is independently hydrogen, $(C_1-C_{10})$alkyl, $(C_1-C_{10})$alkoxy, phenyl, benzyl, phenethyl, or $(C_1-C_{10})$alkanoyl;
each $R_h$ is independently $(C_1-C_{10})$alkyl, phenyl, aryl $(C_1-C_6)$alkyl, heterocycle, or heterocycle$(C_1-C_6)$alkyl;
$R_i$ is hydrogen or $(C_1-C_6)$alkyl; and
$R_j$ and $R_k$ are each independently hydrogen, halo, cyano, nitro, aryl, heterocycle, $(C_2-C_6)$alkenyl, —COOR$_e$, —C(=O)NR$_f$R$_g$, —OC(=O)NR$_f$R$_g$, NR$_f$R$_g$, or —S(O)$_n$R$_h$;
wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, or $(C_1-C_{10})$alkoxycarbonyl of $R_7$, $R_8$, $R_j$ and $R_k$ is optionally substituted with one or more substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$alkanoyloxy, aryloxy, (heterocycle)oxy, $(C_3-C_8)$cycloalkyl, —COOR$_e$, —C(=O)NR$_f$R$_g$, —OC(=O)NR$_f$R$_g$, NR$_h$R$_i$, or —S(O)$_n$R$_k$; and
wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —COOR$_e$, —C(=O)NR$_f$R$_g$, —OC(=O)NR$_f$R$_g$, NR$_f$R$_g$, NR$_h$R$_i$, or—S(O)$_n$R$_k$;

or a pharmaceutically acceptable salt thereof.

22. A method comprising inhibiting a β-lactamase by contacting said β-lactamase with an effective amount of a compound of formula I:

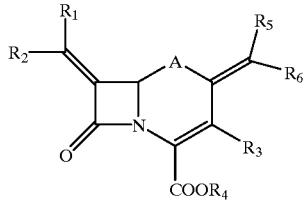

(I)

wherein:

$R_1$, $R_2$, $R_5$, and $R_6$ are each independently hydrogen, $(C_1-C_{10})$alkyl, $(C_2-C_{10})$alkenyl, $(C_2-C_{10})$alkynyl, ($C_3$–$C_8$)cycloalkyl, ($C_1$–$C_{10}$)alkoxy, ($C_1$–$C_{10}$)alkanoyl, ($C_1$–$C_{10}$)alkanoyloxy, ($C_1$–$C_{10}$)alkoxycarbonyl, aryl, heterocycle, halo, cyano, nitro, —COOR$_a$, —C(=O)NR$_b$R$_c$, —OC(=O)NR$_b$R$_c$, NR$_b$R$_c$, or —S(O)$_n$R$_d$; or R$_1$ and R$_2$ together with the carbon to which they are attached are ($C_3$–$C_8$) cycloalkyl or a heterocycle, wherein each ($C_3$–$C_8$) cycloalklyl or heterocycle is optionally substituted with ($C_1$–$C_{10}$)alkyl, hydroxy, halo, ($C_1$–$C_{10}$)alkoxy, ($C_1$–$C_{10}$)alkanoyloxy, or ($C_1$–$C_{10}$)alkoxycarbonyl; or R$_5$ and R$_6$ together with the carbon to which they are attached are ($C_3$–$C_8$)cycloalkyl or a heterocycle, wherein each ($C_3$–$C_8$)cycloalkyl or heterocycle is optionally substituted with ($C_1$–$C_{10}$)alkyl, hydroxy, halo, ($C_1$–$C_{10}$)alkoxy, ($C_1$–$C_{10}$)alkanoyloxy, or ($C_1$–$C_{10}$)alkoxycarbonyl;

R$_3$ is hydrogen, ($C_1$–$C_{10}$)alkyl, ($C_2$–$C_{10}$)alkenyl, ($C_2$–$C_{10}$) alkynyl, ($C_3$–$C_8$)cycloalkyl, ($C_1$–$C_{10}$)alkoxy, ($C_1$–$C_{10}$) alkanoyl, ($C_1$–$C_{10}$)alkanoyloxy, ($C_1$–$C_{10}$) alkoxycarbonyl, halo, cyano, nitro, aryl, heterocycle, —COOR$_a$, —C(=O)NR$_b$R$_c$, —OC(=O)NR$_b$R$_c$, NR$_b$R$_c$, or —S(O)$_n$R$_d$;

R$_4$ is hydrogen;

A is thio, sulfinyl, or sulfonyl;

each n is independently 0, 1, or 2;

each R$_a$ is independently hydrogen, or ($C_1$–$C_{10}$)alkyl;

each R$_b$ and R$_c$ is independently hydrogen, ($C_1$–$C_{10}$) alkyl, ($C_1$–$C_{10}$)alkoxy, phenyl, benzyl, phenethyl, or ($C_1$–$C_{10}$)alkanoyl;

each R$_d$ is independently ($C_1$–$C_{10}$)alkyl, ($C_1$–$C_{10}$) alkanoyl, aryl, heterocycle, aryl($C_1$–$C_6$)alkyl, heterocycle, or heterocycle($C_1$–$C_6$)alkyl;

wherein any ($C_1$–$C_{10}$)alkyl, ($C_2$–$C_{10}$)alkenyl, ($C_2$–$C_{10}$)alkynyl, ($C_3$–$C_8$)cycloalkyl, ($C_1$–$C_{10}$) alkoxy, ($C_1$–$C_{10}$)alkanoyl, ($C_1$–$C_{10}$)alkanoyloxy, or ($C_1$–$C_{10}$)alkoxycarbonyl of R$_1$, R$_2$, R$_3$, R$_5$, and R$_6$ is optionally substituted with one or more substituents independently selected from halo, hydroxy, cyano, cyanato, nitro, mercapto, oxo, aryl, heterocycle, ($C_2$–$C_6$)alkenyl, ($C_2$–$C_6$) alkynyl, ($C_1$–$C_6$)alkoxy, ($C_1$–$C_6$)alkanoyl, ($C_1$–$C_6$)alkanoyloxy, aryl($C_1$–$C_6$)alkanoyloxy, halo($C_1$–$C_6$)alkanoyloxy, heterocycle($C_1$–$C_6$) alkanoyloxy, aryloxy, (heterocycle)oxy, —COOR$_a$, ($C_3$–$C_8$)cycloalkyl, —C(=O)NR$_b$R$_c$, —OC(=O)NR$_b$R$_c$, NR$_b$R$_c$, and —S(O)$_n$R$_d$; and wherein any aryl is optionally substituted with one or more substituents independently selected from halo, hydroxy, cyano, trifluoromethyl, nitro, trifluoromethoxy, ($C_1$–$C_6$)alkyl, ($C_1$–$C_6$)alkanoyl, ($C_1$–$C_6$)alkanoyloxy, ($C_1$–$C_6$)alkoxycarbonyl, —COOR$_a$, —C(=O)NR$_b$R$_c$, —OC(=O)NR$_b$R$_c$, NR$_b$R$_c$, and —S(O)$_n$R$_d$;

or a pharmaceutically acceptable salt thereof.

23. A therapeutic method comprising inhibiting a β-lactamase in a mammal in need of such therapy, by administering an effective inhibitory amount of a compound of formula I:

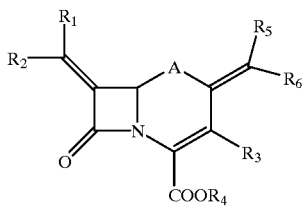

wherein:

R$_1$, R$_2$, R$_5$, and R$_6$ are each independently hydrogen, ($C_1$–$C_{10}$)alkyl, ($C_2$–$C_{10}$)alkenyl, ($C_2$–$C_{10}$)alkynyl, ($C_3$–$C_8$)cycloalkyl, ($C_1$–$C_{10}$)alkoxy, ($C_1$–$C_{10}$) alkanoyl, ($C_1$–$C_{10}$)alkanoyloxy, ($C_1$–$C_{10}$) alkoxycarbonyl, aryl, heterocycle, halo, cyano, nitro, —COOR$_a$, —C(=O)NR$_b$R$_c$, —OC(=O)NR$_b$R$_c$, NR$_b$R$_c$, or —S(O)$_n$R$_d$; or R$_1$ and R$_2$ together with the carbon to which they are attached are ($C_3$–$C_8$) cycloalkyl or a heterocycle, wherein each ($C_3$–$C_8$) cycloalkyl or heterocycle is optionally substituted with ($C_1$–$C_{10}$)alkyl, hydroxy, halo, ($C_1$–$C_{10}$)alkoxy, ($C_1$–$C_{10}$)alkanoyloxy, or ($C_1$–$C_{10}$)alkoxycarbonyl; or R$_5$ and R$_6$ together with the carbon to which they are attached are ($C_3$–$C_8$)cycloalkyl or a heterocycle, wherein each ($C_3$–$C_8$)cycloalkyl or heterocycle is optionally substituted with ($C_1$–$C_{10}$)alkyl, hydroxy, halo, ($C_1$–$C_{10}$)alkoxy, ($C_1$–$C_{10}$)alkanoyloxy, or ($C_1$–$C_{10}$)alkoxycarbonyl;

R$_3$ is hydrogen, ($C_1$–$C_{10}$)alkyl, ($C_2$–$C_{10}$)alkenyl, ($C_2$–$C_{10}$)alkynyl, ($C_3$–$C_8$)cycloalkyl, ($C_1$–$C_{10}$)alkoxy, ($C_1$–$C_{10}$)alkanoyl, ($C_1$–$C_{10}$)alkanoyloxy, ($C_1$–$C_{10}$) alkoxycarbonyl, halo, cyano, nitro, aryl, heterocycle, —COOR$_a$, —C(=O)NR$_b$R$_c$, —OC(=O)NR$_b$R$_c$, NR$_b$R$_c$, or —S(O)$_n$R$_d$;

R$_4$ is hydrogen;

A is thio, sulfinyl, or sulfonyl;

each n is independently 0, 1, or 2;

each R$_a$ is independently hydrogen, or ($C_1$–$C_{10}$)alkyl;

each R$_b$ and R$_c$ is independently hydrogen, ($C_1$–$C_{10}$) alkyl, ($C_1$–$C_{10}$)alkoxy, phenyl, benzyl, phenethyl, or ($C_1$–$C_{10}$)alkanoyl;

each R$_d$ is independently ($C_1$–$C_{10}$)alkyl, ($C_1$–$C_{10}$) alkanoyl, aryl, heterocycle, aryl($C_1$–$C_6$)alkyl, heterocycle, or heterocycle($C_1$–$C_6$)alkyl;

wherein any ($C_1$–$C_{10}$)alkyl, ($C_2$–$C_{10}$)alkenyl, ($C_2$–$C_{30}$)alkynyl, ($C_3$–$C_8$)cycloalkyl, ($C_1$–$C_{10}$) alkoxy, ($C_1$–$C_{10}$)alkanoyl, ($C_1$–$C_{10}$)alkanoyloxy, or ($C_1$–$C_{10}$)alkoxycarbonyl of R$_1$, R$_2$, R$_3$, R$_5$, and R$_6$ is optionally substituted with one or more substituents independently selected from halo, hydroxy, cyano, cyanato, nitro, mercapto, oxo, aryl, heterocycle, ($C_2$–$C_6$)alkenyl, ($C_2$–$C_6$) alkynyl, ($C_1$–$C_6$)alkoxy, ($C_1$–$C_6$)alkanoyl, ($C_1$–$C_6$)alkanoyloxy, aryl($C_1$–$C_6$)alkanoyloxy, halo($C_1$–$C_6$)alkanoyloxy, heterocycle($C_1$–$C_6$) alkanoyloxy, aryloxy, (heterocycle)oxy, —COOR$_a$, ($C_3$–$C_8$)cycloalkyl, —C(=O)NR$_b$R$_c$, —OC(=O)NR$_b$R$_c$, NR$_b$R$_c$, and —S(O)$_n$R$_d$; and wherein any aryl is optionally substituted with one or more substituents independently selected from halo, hydroxy, cyano, trifluoromethyl, nitro, trifluoromethoxy, ($C_1$–$C_6$)alkyl, ($C_1$–$C_6$)alkanoyl, ($C_1$–$C_6$)alkanoyloxy, ($C_1$–$C_6$)alkoxycarbonyl, —COOR$_a$, —C(=O)NR$_b$R$_c$, —OC(=O)NR$_b$R$_c$, NR$_b$R$_c$, and —S(O)$_n$R$_d$;
or a pharmaceutically acceptable salt thereof.

24. A compound of formula IV

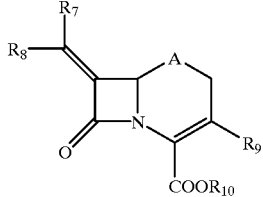

(IV)

wherein:
R$_7$ and R$_8$ are each independently hydrogen, (C$_1$-C$_{10}$)alkyl, (C$_2$-C$_{10}$)alkenyl, (C$_2$-C$_{10}$)alkynyl, (C$_3$-C$_8$)cycloalkyl, (C$_1$-C$_{10}$)alkoxy, (C$_1$-C$_{10}$)alkanoyl, (C$_1$-C$_{10}$)alkanoyloxy, (C$_1$-C$_{10}$)alkoxycarbonyl, aryl, heterocycle, halo, cyano, nitro, —COOR$_e$, —C(=O)NR$_f$R$_g$, —OC(=O)NR$_f$R$_g$, NR$_f$R$_g$, or —S(O)nRh;
R$_9$ is cyano, —CH=NOR$_i$, or a radical of the following formula:

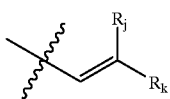

R$_{10}$ is (C$_1$-C$_{10}$)alkyl, (C$_2$-C$_{10}$)alkenyl, (C$_3$-C$_8$)cycloalkyl, (C$_2$-C$_{10}$)alkynyl, aryl, benzyl, and benzhydryl;
A is thio, sulfinyl, or sulfonyl;
each n is independently 0, 1, or 2;
each R$_e$ is independently hydrogen, or (C$_1$-C$_{10}$)alkyl;
each R$_f$ and R$_g$ is independently hydrogen, (C$_1$-C$_{10}$)alkyl, (C$_1$-C$_{10}$)alkoxy, phenyl, benzyl, phenethyl, or (C$_1$-C$_{10}$)alkanoyl;
each R$_h$ is independently (C$_1$-C$_{10}$)alkyl, phenyl, aryl (C$_1$-C$_6$)alkyl, heterocycle, or heterocycle(C$_1$-C$_6$)alkyl;
R$_i$ is hydrogen or (C$_1$-C$_6$)alkyl; and
R$_j$ and R$_k$ are each independently hydrogen, halo, cyano, nitro, aryl, heterocycle, (C$_2$-C$_6$)alkenyl, —COOR$_e$, —C(=O)NR$_f$R$_g$, —OC(=O)NR$_f$R$_g$, NR$_f$R$_g$, or —S(O)$_n$R$_h$;
wherein any (C$_1$-C$_{10}$)alkyl, (C$_2$-C$_{10}$)alkenyl, (C$_2$-C$_{10}$)alkynyl, (C$_3$-C$_8$)cycloalkyl, (C$_1$-C$_{10}$)alkoxy, (C$_1$-C$_{10}$)alkanoyl, (C$_1$-C$_{10}$)alkanoyloxy, or (C$_1$-C$_{10}$)alkoxycarbonyl of R$_7$, R$_8$, R$_j$ and R$_k$ is optionally substituted with one or more substituents independently selected from halo, hydroxy, cyano, cyanato, nitro, mercapto, oxo, aryl, heterocycle, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, aryl(C$_1$-C$_6$)alkanoyloxy, halo(C$_1$-C$_6$)alkanoyloxy, heterocycle(C$_1$-C$_6$)alkanoyloxy, aryloxy, (heterocycle)oxy, (C$_3$-C$_8$)cycloalkyl, —COOR$_e$, —C(=O)NR$_f$R$_g$, —OC(=O)NR$_f$R$_g$, NR$_h$R$_i$, or —S(O)$_n$R$_k$; and
wherein any aryl is optionally substituted with one or more substituents independently selected from halo, hydroxy, cyano, trifluoromethyl, nitro, trifluoromethoxy, (C$_1$-C$_6$)alkyl, (C$_1$-C$_6$)alkanoyl, (C$_1$-C$_6$)alkanoyloxy, (C$_1$-C$_6$)alkoxycarbonyl, —COOR$_e$, —C(=O)NR$_f$R$_g$, —OC(=O)NR$_f$R$_g$, NR$_h$R$_i$, or —S(O)$_n$R$_k$.

25. A compound of formula I:

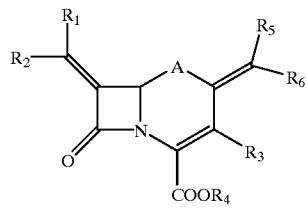

(I)

wherein:
R$_1$, R$_2$, R$_5$, and R$_6$ are each independently hydrogen, (C$_1$-C$_{10}$)alkyl, (C$_2$-C$_{10}$)alkenyl, (C$_2$-C$_{10}$)alkynyl, (C$_3$-C$_8$)cycloalkyl, (C$_1$-C$_{10}$)alkoxy, (C$_1$-C$_{10}$)alkanoyl, (C$_1$-C$_{10}$)alkanoyloxy, (C$_1$-C$_{10}$)alkoxycarbonyl, aryl, heterocycle, halo, cyano, nitro, —COOR$_a$, —C(=O)NR$_b$R$_c$, —OC(=O)NR$_b$R$_c$, NR$_b$R$_c$, or —S(O)$_n$R$_d$; or R$_1$ and R$_2$ together with the carbon to which they are attached are (C$_3$-C$_8$)cycloalkyl or a heterocycle, wherein each (C$_3$-C$_8$)cycloalkyl or heterocycle is optionally substituted with (C$_1$-C$_{10}$)alkyl, hydroxy, halo, (C$_1$-C$_{10}$)alkoxy, (C$_1$-C$_{10}$)alkanoyloxy, or (C$_1$-C$_{10}$)alkoxycarbonyl; or R$_5$ and R$_6$ together with the carbon to which they are attached are (C$_3$-C$_8$)cycloalkyl or a heterocycle, wherein each (C$_3$-C$_8$)cycloalkyl or heterocycle is optionally substituted with (C$_1$-C$_{10}$)alkyl, hydroxy, halo, (C$_1$-C$_{10}$)alkoxy, (C$_1$-C$_{10}$)alkanoyloxy, or (C$_1$-C$_{10}$)alkoxycarbonyl;
R$_3$ is hydrogen, (C$_1$-C$_{10}$)alkyl, (C$_2$-C$_{10}$)alkenyl, (C$_2$-C$_{10}$)alkynyl, (C$_3$-C$_8$)cycloalkyl, (C$_1$-C$_{10}$)alkoxy, (C$_1$-C$_{10}$)alkanoyl, (C$_1$-C$_{10}$)alkanoyloxy, (C$_1$-C$_{10}$)alkoxycarbonyl, halo, cyano, nitro, aryl, heterocycle, —COOR$_a$, —C(=O)NR$_b$R$_c$, —OC(=O)NR$_b$R$_c$, NR$_b$R$_c$, or —S(O)$_n$R$_d$;
R$_4$ is (C$_1$-C$_{10}$)alkyl, (C$_2$-C$_{10}$)alkenyl, (C$_3$-C$_8$)cycloalkyl, (C$_2$-C$_{10}$)alkynyl, aryl, benzyl, and benzhydryl;
A is thio, sulfinyl, or sulfonyl;
each n is independently 0, 1, or 2;
each R$_a$ is independently hydrogen, or (C$_1$-C$_{10}$)alkyl;
each R$_b$ and R$_c$ is independently hydrogen, (C$_1$-C$_{10}$)alkyl, (C$_1$-C$_{10}$)alkoxy, phenyl, benzyl, phenethyl, or (C$_1$-C$_{10}$)alkanoyl;
each R$_d$ is independently (C$_1$-C$_{10}$)alkyl, (C$_1$-C$_{10}$)alkanoyl, aryl, heterocycle, aryl(C$_1$-C$_6$)alkyl, heterocycle, or heterocycle(C$_1$-C$_6$)alkyl;
wherein any (C$_1$-C$_{10}$)alkyl, (C$_2$-C$_{10}$)alkenyl, (C$_2$-C$_{10}$)alkynyl, (C$_3$-C$_8$)cycloalkyl, (C$_1$-C$_{10}$)alkoxy, (C$_1$-C$_{10}$)alkanoyl, (C$_1$-C$_{10}$)alkanoyloxy, or (C$_1$-C$_{10}$)alkoxycarbonyl of R$_1$, R$_2$, R$_3$, R$_5$, and R$_6$ is optionally substituted with one or more substituents independently selected from halo, hydroxy, cyano, cyanato, nitro, mercapto, oxo, aryl, heterocycle, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, aryl(C$_1$-C$_6$)alkanoyloxy, halo(C$_1$-C$_6$)alkanoyloxy, heterocycle(C$_1$-C$_6$)alkanoyloxy, aryloxy, (heterocycle)oxy, —COOR$_a$, (C$_3$-C$_8$)cycloalkyl, —C(=O)NR$_b$R$_c$, —OC(=O)NR$_b$R$_c$, NR$_b$R$_c$, and —S(O)$_n$R$_d$; and wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —COOR$_a$, —C(=O)NR$_b$R$_c$, —OC(=O)NR$_b$R$_c$, NR$_b$R$_c$, and —S(O)$_n$R$_d$.

26. A compound of formula IV:

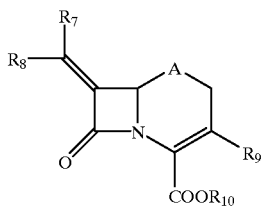

wherein:
R$_7$ and R$_8$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$;

R$_9$ is cyano, —CH=NOR$_i$, or a radical of the following formula

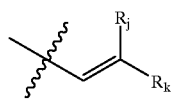

R$_{10}$ is hydrogen;
A is thio, sulfinyl, or sulfonyl;
each n is independently 0, 1, or 2;
each R$_e$ is independently hydrogen, or $(C_1-C_{10})$alkyl;
each R$_f$ and R$_g$ is independently hydrogen, $(C_1-C_{10})$alkyl, $(C_1-C_{10})$alkoxy, phenyl, benzyl, phenethyl, or $(C_1-C_{10})$alkanoyl;
each R$_h$ is independently $(C_1-C_{10})$alkyl, phenyl, aryl $(C_1-C_6)$alkyl, heterocycle, or heterocycle$(C_1-C_6)$alkyl;
R$_i$ is hydrogen or $(C_1-C_6)$alkyl; and
R$_j$ and R$_k$ are each independently hydrogen, halo, cyano, nitro, aryl, heterocycle, $(C_2-C_6)$alkenyl, —COOR$_e$, —C(=O)NR$_f$R$_g$, —OC(=O)NR$_f$R$_g$, NR$_f$R$_g$, or —S(O)$_n$R$_h$;
wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, or $(C_1-C_{10})$alkoxycarbonyl of R$_7$, R$_8$, R$_j$ and R$_k$ is optionally substituted with one or more substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, aryl$(C_1-C_6)$alkanoyloxy, halo $(C_1-C_6)$alkanoyloxy, heterocycle$(C_1-C_6)$alkanoyloxy, aryloxy, (heterocycle)oxy, $(C_3-C_8)$cycloalkyl, —COOR$_e$, —C(=O)NR$_f$R$_g$, —OC(=O)NR$_f$R$_g$, NR$_h$R$_i$, or —S(O)$_n$R$_k$; and
wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —COOR$_e$, —C(=O)NR$_f$R$_g$, —OC(=O)NR$_f$R$_g$, NR$_h$R$_i$, or —S(O)$_n$R$_k$;

or a pharmaceutically acceptable salt thereof.

27. The compound of claim 26 wherein R$_7$ is aryl, heterocycle, or —COOR$_e$.

28. The compound of claim 26 wherein R$_7$ is 2-pyridyl, or —COOR$_e$.

29. The compound of claim 26 wherein R$_8$ is hydrogen.

30. The compound of claim 26 wherein one of R$_j$ and R$_k$ is hydrogen and the other is cyano, —COOR$_e$, $(C_2-C_{10})$alkenyl, or heteroaryl.

31. The compound of claim 26 wherein R$_j$ is hydrogen or halo, and R$_k$ is cyano, methoxycarbonyl, aminocarbonyl, tert-butoxycarbonyl, 2-pyridyl-N-oxide, nitro, or vinyl.

32. The compound of claim 26 which is a pharmaceutically acceptable salt of a compound of formula IV wherein R$_{11}$ is hydrogen.

33. The compound of claim 26 wherein A is sulfonyl.

34. The compound of claim 26 wherein A is sulfonyl; R$_7$ is 2-pyridyl, carboxy or tert-butoxy carbonyl; R$_8$ is hydrogen; R$_j$ is hydrogen or halo; and R$_k$ is cyano, methoxycarbonyl, aminocarbonyl, tert-butoxycarbonyl, 2-pyridyl-N-oxide, nitro, or vinyl.

35. A pharmaceutical composition comprising a compound of formula IV:

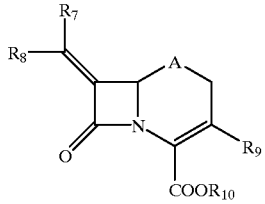

wherein:
R$_7$ and R$_8$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$;

R$_9$ is cyano, —CH=NOR$_i$, or a radical of the following formula

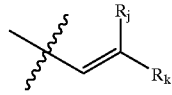

R$_{10}$ is hydrogen;
A is thio, sulfinyl, or sulfonyl;
each n is independently 0, 1, or 2;
each R$_e$ is independently hydrogen, or $(C_1-C_{10})$alkyl;
each R$_f$ and R$_g$ is independently hydrogen, $(C_1-C_{10})$alkyl, $(C_1-C_{10})$alkoxy, phenyl, benzyl, phenethyl, or $(C_1-C_{10})$alkanoyl;
each R$_h$ is independently $(C_1-C_{10})$alkyl, phenyl, aryl $(C_1-C_6)$alkyl, heterocycle, or heterocycle$(C_1-C_6)$alkyl;
R$_i$ is hydrogen or $(C_1-C_6)$alkyl; and $R_j$ and $R_k$ are each independently hydrogen, halo, cyano, nitro, aryl, heterocycle, $(C_2-C_6)$alkenyl, —COOR$_e$, —C(=O)NR$_f$R$_g$, —OC(=O)NR$_f$R$_g$, NR$_f$R$_g$, or —S(O)$_n$R$_h$;

wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, or $(C_1-C_{10})$alkoxycarbonyl of $R_7$, $R_8$, $R_j$ and $R_k$ is optionally substituted with one or more substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$alkanoyloxy, aryloxy, (heterocycle)oxy, $(C_3-C_8)$cycloalkyl, —COOR$_e$, —C(=O)NR$_f$R$_g$, —OC(=O)NR$_f$R$_g$, NR$_h$R$_i$, or —S(O)$_n$R$_k$; and wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —COOR$_e$, —C(=O)NR$_f$R$_g$, —OC(=O)NR$_f$R$_g$, NR$_h$R$_i$, or —S(O)$_n$R$_k$;

or a pharmaceutically acceptable salt thereof; and a pharmaceutically acceptable carrier.

* * * * *

UNITED STATES PATENT AND TRADEMARK OFFICE
CERTIFICATE OF CORRECTION

PATENT NO. : 6,407,091 B1
DATED : June 18, 2002
INVENTOR(S) : John D. Buynak, A. Srinivasa Rao, Greg C. Adam, Sirishkumar D. Nidamarthy and Venkata Ramana Doppalapudi It is certified that error appears in the above-identified patent and that said Letters Patent is hereby corrected as shown below:

Column 33,
Line 27, delete "2-pyridiyl" and insert -- 2-pyridyl --, therefor.

Column 38,
Line 50, delete "$(C_2-C_{30})$alkynyl" and insert -- $(C_2-C_{10})$alkynyl --, therefor.

Column 35,
Line 20, delete "[(e.g. 1, 2, 3, or 4) ]".
Line 32, delete "[(e.g. 1, 2, 3, or 4)]".

Signed and Sealed this

Twelfth Day of November, 2002

Attest:

Attesting Officer

JAMES E. ROGAN
Director of the United States Patent and Trademark Office